United States Patent
Ando et al.

(10) Patent No.: US 8,394,891 B2
(45) Date of Patent: Mar. 12, 2013

(54) ADDITIVE FOR POLYMERIZABLE COMPOSITION, POLYMERIZABLE COMPOSITION CONTAINING THE SAME AND USE OF THE POLYMERIZABLE COMPOSITION

(75) Inventors: Tomoyuki Ando, Omuta (JP); Seiichi Kobayashi, Omuta (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 289 days.

(21) Appl. No.: 12/811,713

(22) PCT Filed: Dec. 11, 2008

(86) PCT No.: PCT/JP2008/003703
§ 371 (c)(1),
(2), (4) Date: Jul. 6, 2010

(87) PCT Pub. No.: WO2009/087717
PCT Pub. Date: Jul. 16, 2009

(65) Prior Publication Data
US 2010/0286334 A1    Nov. 11, 2010

(30) Foreign Application Priority Data

Jan. 10, 2008  (JP) ................... 2008-002899
Aug. 13, 2008  (JP) ................... 2008-208615

(51) Int. Cl.
*C08K 5/37*    (2006.01)
*C07F 9/90*    (2006.01)
*C07F 7/22*    (2006.01)

(52) U.S. Cl. ............... 524/750; 556/76; 556/81
(58) Field of Classification Search ............ 524/750; 556/76, 81
See application file for complete search history.

(56) References Cited

U.S. PATENT DOCUMENTS

| | | | |
|---|---|---|---|
| 2007/0191615 A1 | 8/2007 | Otsuji et al. | |
| 2009/0076208 A1 | 3/2009 | Usugi et al. | |
| 2010/0063246 A1 | 3/2010 | Usugi et al. | |

FOREIGN PATENT DOCUMENTS

| | | |
|---|---|---|
| EP | 0 370 164 A2 | 5/1990 |
| GB | 712828 | 8/1954 |
| JP | 61-217063 A | 9/1986 |
| JP | 61-258272 A | 11/1986 |
| JP | 63-297376 A | 12/1988 |
| JP | 2003-327583 A | 11/2003 |
| JP | 2006-143782 A | 6/2006 |
| JP | 2007-269648 A | 10/2007 |
| JP | 2007-269649 A | 10/2007 |
| JP | 2007-271744 A | 10/2007 |
| WO | WO 2005/095490 A1 | 10/2005 |
| WO | WO 2007/099702 A1 | 9/2007 |
| WO | WO 2007/125636 A1 | 11/2007 |
| WO | WO 2007/148439 A1 | 12/2007 |

OTHER PUBLICATIONS

Kricheldorf et al., Macromolecules, vol. 29, No. 5, pp. 1375-1381 (date: Feb. 26, 1996).*
International Search Report for PCT/JP2008/003703 completed Feb. 26, 2009.
Journal of the Chemical Society, 1965, pp. 7098-7102.
Extended European Search Report dated Feb. 23, 2012, issued by the European Patent Office in the corresponding European Application No. 08870095.0. (11 pages).
Kricheldorf et al., "Polylactones 36. Macrocyclic Polymerization of Lactides with Cyclic Bu$_2$Sn Initiators Derived from 1,2-Ethanediol, 2-Mercaptoethanol, and 1,2-Dimercaptoethane", Macromolecules, (Feb. 26, 1996), vol. 29, Issue 5, pp. 1375-1381.
Al-Masri et al., "New Polymer Syntheses. 105. Syntheses of Aliphatic Poly (Thioester)s by Ring-opening Polycondensation of 2,2-Dibutyl-2-Stanna-1.3-Dithiolane", J.Macromol. Sci.—Pure Appl. Chem., (Jan. 2001), vol. A38, Issue 10, pp. 1007-1017.
Buys et al., "Novel Catalyst Systems, Based on Organozinc Compounds and Group IVB Organometallic Compounds, for the Stereospecific Polymerization of Oxiranes", Polymer Science and Technology, (Jan. 1983), vol. 19, pp. 75-94.

* cited by examiner

*Primary Examiner* — Robert D. Harlan
(74) *Attorney, Agent, or Firm* — Buchanan Ingersoll & Rooney PC

(57) ABSTRACT

The additive for a polymerizable composition according to the present invention contains a compound represented by the general formula (a). In the general formula (a), R represents a saturated hydrocarbon group having 1 to 3 carbon atoms. M represents Sn, Sb, Bi, or Ge. m represents 0 or 1. R and M are not directly bonded when m is 0. n represents an integer of 1 to 3. X represents a monovalent linking group, and a plurality of X may be the same as or different from each other. When two or more linking groups X are bonded with the metal atom M, the linking groups X may combine together to form a ring.

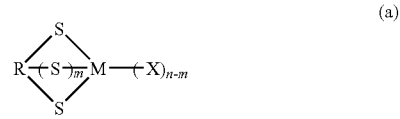

(a)

23 Claims, No Drawings

ADDITIVE FOR POLYMERIZABLE COMPOSITION, POLYMERIZABLE COMPOSITION CONTAINING THE SAME AND USE OF THE POLYMERIZABLE COMPOSITION

TECHNICAL FIELD

The present invention relates to an additive for a polymerizable composition, a polymerizable composition containing the same, and use of the polymerizable composition.

BACKGROUND ART

In recent years, a transparent organic polymer material has been used as a transparent material in place of an inorganic glass, and has been employed, for example, in optical components or the like. The optical component is required to have generally required properties such as transparency, thermal properties, mechanical properties as well as a high refractive index.

One of the conventional techniques concerning such a resin is described in Patent Document 1. In this Document, a thietane compound containing a metal is described. In addition, an optical resin having a high refractive index exceeding 1.7 is described.

Patent Document 2 describes a polymerizable composition which includes a compound containing Sn as a common ring-member atom on two hetero rings and a polythiol.

[Patent Document 1] Pamphlet of International Publication No. 2005-095490
[Patent Document 2] Japanese Unexamined Patent Application Publication No. 2006-143782
[Patent Document 3] GB Patent Publication No. 712828
[Patent Document 4] Japanese Unexamined Patent Application Publication No. 2003-327583
[Patent Document 5] Japanese Unexamined Patent Application Publication No. 2007-269648
[Patent Document 6] Japanese Unexamined Patent Application Publication No. 2007-269649
[Patent Document 7] Japanese Unexamined Patent Application Publication No. 2007-271744
[Non-Patent Document 1] Journal of the Chemical Society (1965), 7098-7102

DISCLOSURE OF THE INVENTION

Even the technology described in Patent Document 1 has room for improvement regarding the point of increasing the refractive index of a transparent member obtained from the polymerizable composition.

The present invention relates to the following:

[1] An additive for a polymerizable composition containing a compound represented by the following general formula (a).

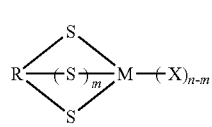

(a)

(In the general formula (a), R represents a saturated hydrocarbon group having 1 to 3 carbon atoms. M represents Sn, Sb, Bi, or Ge. m represents 0 or 1. R and M are not directly bonded when m is 0. n represents an integer of 1 to 3. X represents a monovalent linking group and a plurality of X may be the same as or different from each other. If two or more linking groups X are bonded with the metal atom M, the linking groups X may combine together to form a ring.)

[2] The additive for a polymerizable composition as set forth in [1], wherein the compound represented by the general formula (a) is represented by the following general formula (1).

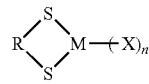

(1)

(In the general formula (1), M represents Sn, Sb, or Bi. R represents an alkylene group having 1 to 3 carbon atoms. n and X are the same as in the general formula (a).)

[3] The additive for a polymerizable composition as set forth in [2], wherein the compound represented by the general formula (1) is represented by the following general formula (2) or (3).

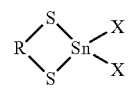

(2)

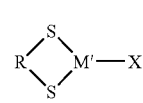

(3)

(In the general formula (2) or (3), R and X are the same as in the general formula (1). In the general formula (2), the two linking groups X may form a ring. In the general formula (3), M' represents Sb or Bi.)

[4] The additive for a polymerizable composition as set forth in [2] or [3], wherein R is an alkylene group having 2 or 3 carbon atoms.

[5] The additive for a polymerizable composition as set forth in [4], wherein the compound represented by the general formula (2) is represented by the following general formula (4) or (5).

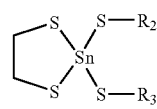

(4)

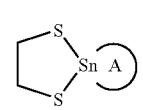

(5)

(In the general formula (4), $R_2$ and $R_3$ each independently represent an alkyl group having 1 to 3 carbon atoms. In the general formula (5), A represents a ring structure.)

[6] The additive for a polymerizable composition as set forth in [5], wherein the compound represented by the general formula (5) is represented by the following general formula (5a) or (5b).

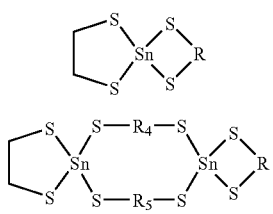
(5a)

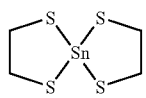
(5b)

(In the general formulae (5a) and (5b), R is the same as in the general formula (1). In the general formula (5b), $R_4$ and $R_5$ represent an alkylene group having 1 to 3 carbon atoms, and may be the same as or different from each other.)

[7] The additive for a polymerizable composition as set forth in [6], wherein the compound represented by the general formula (5a) is represented by the following chemical formula.

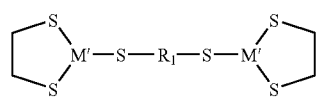

[8] The additive for a polymerizable composition as set forth in [4], wherein the compound represented by the general formula (3) is represented by the following general formula (6).

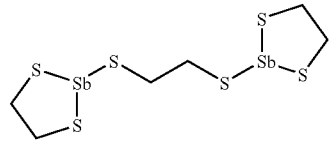
(6)

(In the general formula (6), M' represents Sb or Bi, and $R_1$ represents an alkylene group having 1 to 3 carbon atoms.)

[9] The additive for a polymerizable composition as set forth in [8], wherein M' is Sb.

[10] The additive for a polymerizable composition as set forth in [9], wherein the compound represented by the general formula (6) is represented by the following chemical formula.

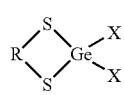

[11] The additive for a polymerizable composition as set forth in [1], wherein the compound represented by the general formula (a) is represented by the following general formula (9).

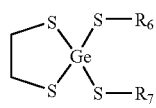
(9)

(In the general formula (9), R represents an alkylene group having 1 to 3 carbon atoms. X is the same as in the general formula (a).)

[12] The additive for a polymerizable composition as set forth in [11], wherein the compound represented by the general formula (9) is represented by the following general formula (10) or (11).

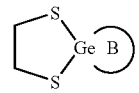
(10)

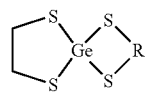
(11)

(In the general formula (10), $R_6$ and $R_7$ each independently represent an alkyl group having 1 to 3 carbon atoms. In the general formula (11), B represents a ring structure.)

[13] The additive for a polymerizable composition as set forth in [12], wherein the compound represented by the general formula (11) is represented by the following general formula (11a) or (11b).

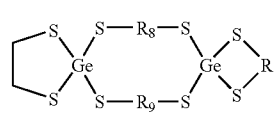
(11a)

(11b)

(In the general formulae (11a) and (11b), R is the same as in the general formula (9). In the general formula (11b), $R_8$ and $R_9$ represent an alkylene group having 1 to 3 carbon atoms, and may be the same as or different from each other.)

[14] The additive for a polymerizable composition as set forth in [13], wherein the compound represented by the general formula (11a) is represented by the following chemical formula.

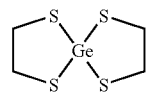

[15] The additive for a polymerizable composition as set forth in [1], wherein the compound represented by the general formula (a) is represented by the following chemical formula.

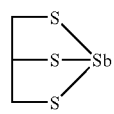

[16] A polymerizable composition, wherein the additive for a polymerizable composition as set forth in any one of [1] to [15] is blended.

[17] The polymerizable composition as set forth in [16], wherein a thiol compound is further blended.

[18] The polymerizable composition as set forth in [17], wherein the thiol compound contains at least one selected from the group consisting of 3-mercaptothietane, 1,2-ethanedithiol, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 1,1,3,3-tetrakis (mercaptomethylthio)propane, 4,6-bis (mercaptomethylthio)-1,3-dithiane, 2-(2,2-bis (mercaptomethylthio)ethyl)-1,3-dithietane, and 2,5-bis (mercaptomethyl)-1,4-dithiane.

[19] The polymerizable composition as set forth in [18], wherein a polymerizable compound is further blended.

[20] The polymerizable composition as set forth in [19], wherein the polymerizable compound contains at least one selected from the group consisting of an isocyanate compound, an episulfide compound, an epoxy compound, and a thietane compound.

[21] A resin obtained by polymerization of the polymerizable composition as set forth in any one of [16] to [20].

[22] A transparent member comprising the resin as set forth in [21].

[23] An optical component comprising the transparent member as set forth in [22].

According to the present invention, an additive (a refractive index enhancer) for a polymerizable composition, which is capable of further improving the refractive index of a transparent member obtained from the polymerizable composition, a polymerizable composition in which the additive is blended, and a transparent member and an optical component, each obtained from the polymerizable composition are provided.

BEST MODE FOR CARRYING OUT THE INVENTION

Hereinbelow, the present invention will be described with reference to specific examples, but the present invention is not intended to be limited thereto.

[Additive for Polymerizable Composition]

The additive for a polymerizable composition of the present invention (also hereinafter referred to as the "additive") contains a compound represented by the following general formula (a).

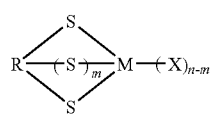

(a)

In the general formula (a), R represents a saturated hydrocarbon group having 1 to 3 carbon atoms. M represents Sn, Sb, Bi, or Ge. m represents 0 or 1. R and M are not directly bonded when m is 0. n represents an integer of 1 to 3. X represents a monovalent linking group and a plurality of X may be the same as or different from each other. If two or more linking groups X are bonded with the metal atom M, the linking groups X may combine together to form a ring.

Thus, the additive of the present invention has no polymerizable functional group (for example, a hydroxyl group (OH group) and a mercapto group (SH group)) in the molecule.

By using the additive for a polymerizable composition of the present invention having such a structure, the refractive indices of the resin and the transparent member can be controlled.

Examples of the metal atom M include a tetravalent Sn, a trivalent or pentavalent Sb, a trivalent or pentavalent Bi, and a tetravalent Ge.

The additive for a polymerizable composition of the present invention preferably contains a compound represented by the following general formula (1) as the compound represented by the general formula (a).

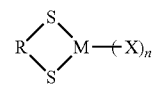

(1)

In the general formula (1), M represents Sn, Sb, or Bi. R represents an alkylene group having 1 to 3 carbon atoms. n and X are the same as in the general formula (a). By using the additive for a polymerizable composition containing the compound represented by the general formula (1), the refractive indices of the resin and the transparent member can be controlled.

Examples of the metal atom M include a tetravalent Sn, a trivalent or pentavalent Sb, and a trivalent or pentavalent Bi.

Examples of the compound represented by the general formula (1) include a compound represented by the following general formula (2) or (3).

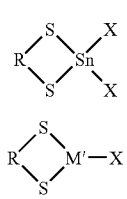

(2)

(3)

In the general formula (2) or (3), R and X are the same as in the general formula (1). In the general formula (2), the two linking groups X may form a ring. In the general formula (3), M' represents Sb or Bi.

From the viewpoint of improvement of the refractive indices of the resin and the transparent member, in the general formula (2) or (3), R is preferably an alkylene group having 2 or 3 carbon atoms, and more preferably an alkylene group having 2 carbon atoms. From the viewpoint of the monomer handleability or the like, in the general formula (3), M' is preferably Sb.

In the general formulae (1) to (3), examples of the monovalent linking group X include an alkyl group having 1 to 3 carbon atoms, an alkylsulfanyl group having 1 to 3 carbon atoms, a group represented by the following general formula (1a), and the like.

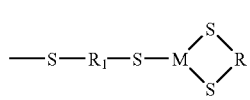

(1a)

In the general formula (1a), R and M are the same as in the general formula (1). In the compound of the general formula (1), if a plurality of R and M are present, they may be the same as or different from each other. $R_1$ represents an alkylene group having 1 to 3 carbon atoms, and in the compound represented by the general formula (1), if a plurality of $R_1$'s are present, they may be the same as or different from each other.

As the compound represented by the general formula (2), a compound represented by the following general formula (4) or (5) can be preferably used.

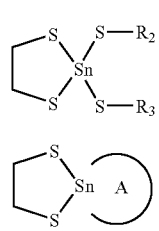

(4)

(5)

In the general formula (4), $R_2$ and $R_3$ each independently represent an alkyl group having 1 to 3 carbon atoms. In the general formula (5), A represents a ring structure.

Examples of the compound of the general formula (5) include the structures represented by the following general formula (5a) or (5b).

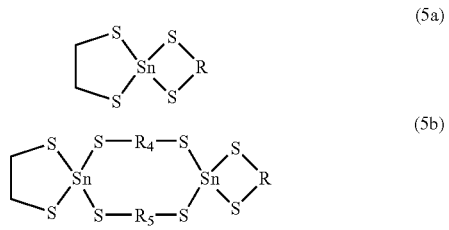

(5a)

(5b)

In the general formulae (5a) and (5b), R is the same as in the general formula (1).

In the general formula (5b), $R_4$ and $R_5$ represent an alkylene group having 1 to 3 carbon atoms, and may be the same as or different from each other.

In the present invention, as the compound represented by the general formula (2), a compound represented by the following chemical formula can be preferably used. By this compound, the refractive indices of the resin and the transparent member can be controlled to facilitate the improvement of the refractive indices.

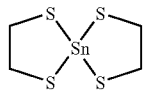

On the other hand, as the compound represented by the general formula (3), a compound represented by the following general formula (6) can be preferably used.

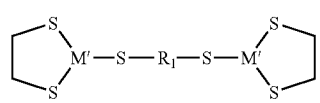

(6)

In the general formula (6), M' represents Sb or Bi, and $R_1$ represents an alkylene group having 1 to 3 carbon atoms.

In the present invention, as the compound represented by the general formula (3), a compound represented by the following chemical formula can be preferably used. By this compound, the refractive indices of the resin and the transparent member can be controlled to facilitate the improvement of the refractive indices. Furthermore, the following compound may contain an isomer.

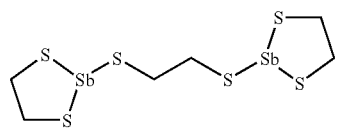

Such a compound represented by the general formula (1) is not particularly limited, and can be prepared by a known method.

The additive for a polymerizable composition of the present invention preferably contains a compound represented by the following general formula (9) as the compound represented by the general formula (a).

(9)

In the general formula (9), R represents an alkylene group having 1 to 3 carbon atoms. X represents a monovalent linking group, and the two X may be the same as or different from each other. The linking groups X may combine together to form a ring. By using such an additive for a polymerizable composition having Ge as a metal atom, the refractive indices of the resin and the transparent member can be controlled.

From the viewpoint of improvement of the refractive index of the resin and the transparent member, in the general formula (9), R is preferably an alkylene group having 2 or 3 carbon atoms, and more preferably an alkylene group having 2 carbon atoms.

As the compound represented by the general formula (9), a compound represented by the following general formula (10) or (11) can be preferably used.

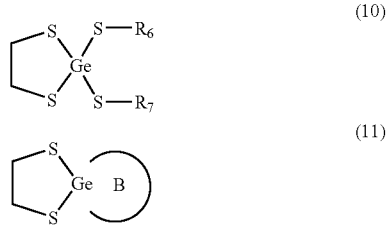

(10)

(11)

In the general formula (10), $R_6$ and $R_7$ each independently represent an alkyl group having 1 to 3 carbon atoms. In the general formula (11), B represents a ring structure.

Examples of the compound of the general formula (11) include a compound represented by the following general formula (11a) or (11b).

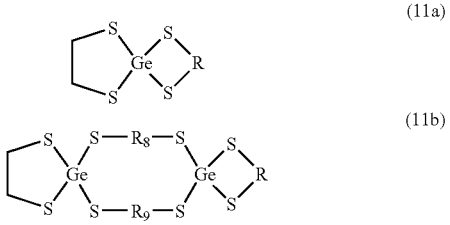
(11a)
(11b)

In the general formulae (11a) and (11b), R is the same as in the general formula (9). In the general formula (11b), $R_8$ and $R_9$ represent an alkylene group having 1 to 3 carbon atoms, and may be the same as or different from each other.

In the present invention, as the compound represented by the general formula (9), the compound represented by the following chemical formula can be preferably used. By this compound, the refractive indices of the resin and the transparent member can be controlled to facilitate the improvement of the refractive indices.

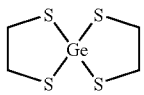

Such a compound represented by the general formula (9) is not particularly limited, and can be prepared by a known method.

The polymerizable composition of the present invention preferably contains a compound represented by the following chemical formula as the compound represented by the general formula (a). By using this compound as an additive, the refractive indices of the resin and the transparent member can be controlled to facilitate the improvement of the refractive indices.

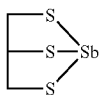

[Polymerizable Composition]

The polymerizable composition of the present invention is formed by blending the additive of the present invention. A transparent member such as, for example, an optical component can be obtained from the polymerizable composition.

The polymerizable composition of the present invention may contain a thiol compound in addition to above-mentioned additive. The additive of the present invention has high compatibility with the thiol compound, and the use in combination with the thiol compound results in a transparent member having excellent transparency and an improved refractive index.

Further, a polymerizable compound other than the thiol compound, which has reactivity with the thiol compound, may be included.

Hereinbelow, the thiol compound and the polymerizable compound contained in the polymerizable composition of the present invention will be described.

(Thiol Compound)

The thiol compound is a compound having one or more thiol groups (SH groups) in the molecule. As the thiol compound, a compound having a structure compatible with the additive can be used.

Specific examples of the thiol compound include the monovalent thiol compound including aliphatic mercaptan compounds such as methyl mercaptan, ethyl mercaptan, propylmercaptan, butyl mercaptan, octyl mercaptan, dodecyl mercaptan, tert-dodecyl mercaptan, hexadecyl mercaptan, octadecyl mercaptan, cyclohexyl mercaptan, benzyl mercaptan, ethyl phenyl mercaptan, 2-mercaptomethyl-1,3-dithiolane, 2-mercaptomethyl-1,4-dithiane, 1-mercapto-2,3-epithiopropane, 1-mercaptomethylthio-2,3-epithiopropane, 1-mercaptoethylthio-2,3-epithiopropane, 3-mercaptothietane, 2-mercaptothietane, 3-mercaptomethylthiothietane, 2-mercaptomethylthiothietane, 3-mercaptoethylthiothietane, 2-mercaptoethylthiothietane; aromatic mercaptan compounds such as thiophenol, mercaptotoluene; and compounds each containing a hydroxy group in addition to the mercapto group, such as 2-mercaptoethanol, 3-mercapto-1,2-propanediol.

Furthermore, examples of the polyvalent thiol (polythiol) compound include aliphatic polythiol compounds such as 1,1-methanedithiol, 1,2-ethanedithiol, 1,1-propanedithiol, 1,2-propanedithiol, 1,3-propanedithiol, 2,2-propanedithiol, 1,6-hexanedithiol, 1,2,3-propanetrithiol, 1,1-cyclohexanedithiol, 1,2-cyclohexanedithiol, 2,2-dimethylpropane-1, 3-dithiol, 3,4-dimethoxybutane-1,2-dithiol, 2-methylcyclohexane-2,3-dithiol, 1,1-bis(mercaptomethyl)cyclohexane, thiomalic acid bis(2-mercaptoethyl ester), 2,3-dimercapto-1-propanol(2-mercaptoacetate), 2,3-dimercapto-1-propanol(3-mercaptopropionate), diethylene glycol bis(2-mercaptoacetate), diethylene glycol bis(3-mercaptopropionate), 1,2-dimercaptopropyl methyl ether, 2,3-dimercaptopropyl methyl ether, 2,2-bis(mercaptomethyl)-1,3-propanedithiol, bis(2-mercaptoethyl)ether, ethylene glycol bis(2-mercaptoacetate), ethylene glycol bis(3-mercaptopropionate), trimethylolpropane bis(2-mercaptoacetate), trimethylolpropane bis(3-mercaptopropionate), pentaerythritol tetrakis(2-mercaptoacetate), pentaerythritol tetrakis(3-mercaptopropionate), tetrakis(mercaptomethyl)methane, 1,1,1,1-tetrakis(mercaptomethyl)methane;

aromatic polythiol compounds such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl)benzene, 1,3,5-tris(mercaptomethyl)benzene, 1,2,3-tris(mercaptoethyl)benzene, 1,2,4-tris(mercaptoethyl)benzene, 1,3,5-tris(mercaptoethyl)benzene, 2,5-toluenedithiol, 3,4-toluenedithiol, 1,3-di(p-methoxy phenyl)propane-2,2-dithiol, 1,3-diphenylpropane-2,2-dithiol, phenyl methane-1, 1-dithiol, 2,4-di(p-mercaptophenyl)pentane;

aromatic polythiol compounds each containing a sulfur atom in addition to the mercapto group, such as 1,2-bis(mercaptoethylthio)benzene, 1,3-bis(mercaptoethylthio)benzene, 1,4-bis(mercaptoethylthio)benzene, 1,2,3-tris(mercaptomethylthio)benzene, 1,2,4-tris(mercaptomethylthio)benzene, 1,3,5-tris(mercaptomethylthio)benzene, 1,2,3-tris(mercaptoethylthio)benzene, 1,2,4-tris(mercaptoethylthio)benzene, 1,3,5-tris(mercaptoethylthio)benzene, and core alkylated compounds thereof;

aliphatic polythiol compounds each containing a sulfur atom in addition to the mercapto group, such as bis(mercaptomethyl)sulfide, bis(mercaptomethyl)disulfide, bis(mercaptoethyl)sulfide, bis(mercaptoethyl)disulfide, bis(mercaptopropyl)sulfide, bis(mercaptomethylthio)methane, bis(2-mercaptoethylthio)methane, bis(3-mercaptopropylthio)

methane, 1,2-bis(mercaptomethylthio)ethane, 1,2-bis(2-mercaptoethylthio)ethane, 1,2-bis(3-mercaptopropyl)ethane, 1,3-bis(mercaptomethylthio)propane, 1,3-bis(2-mercaptoethylthio)propane, 1,3-bis(3-mercaptopropylthio)propane, 1,2,3-tris(mercaptomethylthio)propane, 1,2,3-tris(2-mercaptoethylthio)propane, 1,2,3-tris(3-mercaptopropylthio)propane, 1,2-bis[(2-mercaptoethyl)thio]-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl)sulfide, bis(1,3-dimercaptopropyl)sulfide, 2,5-dimercapto-1,4-dithiane, 2,5-bis(mercaptomethyl)-1,4-dithiane, 2,5-dimercaptomethyl-2,5-dimethyl-1,4-dithiane, bis(mercaptomethyl)disulfide, bis(mercaptoethyl)disulfide, bis(mercaptopropyl)disulfide, 4-mercaptomethyl-1,8-dimercapto-3,6-dithiaoctane, and thioglycolates thereof and esters which are obtained by reacting those aliphatic polythiols with mercaptopropionates;

aliphatic polythiol compounds each having an ester bond and a sulfur atom in addition to the mercapto group, such as hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxy propyl sulfide bis(2-mercaptoacetate), hydroxy propyl sulfide bis(3-mercaptopropionate), hydroxymethyldisulfide bis(2-mercaptoacetate), hydroxymethyldisulfide bis(3-mercaptopropionate), hydroxyethyldisulfide bis(2-mercaptoacetate), hydroxyethyldisulfide bis(3-mercaptopropionate), hydroxypropyldisulfide bis(2-mercaptoacetate), hydroxypropyldisulfide bis(3-mercaptopropionate), 2-mercaptoethyl ether bis(2-mercaptoacetate), 2-mercaptoethyl ether bis(3-mercaptopropionate), 1,4-dithiane-2,5-diol bis(2-mercaptoacetate), 1,4-dithiane-2,5-diol bis(3-mercaptopropionate), thiodiglycolic acid bis(2-mercaptoethyl ester), thiodipropionic acid bis(2-mercaptoethyl ester), 4,4-thiodibutyric acid bis(2-mercaptoethyl ester), dithiodiglycolic acid bis(2-mercaptoethyl ester), dithiodipropionic acid bis(2-mercaptoethyl ester), 4,4-dithiodibutyric acid bis(2-mercaptoethyl ester), thiodiglycolic acid bis(2,3-dimercaptopropyl ester), thiodipropionic acid bis(2,3-dimercaptopropyl ester), dithiodiglycolic acid bis(2,3-dimercaptopropyl ester), dithiodipropionic acid bis(2,3-dimercaptopropyl ester);

heterocyclic compounds each containing a sulfur atom in addition to the mercapto group, such as 3,4-thiophenedithiol, 2,5-dimercapto-1,3,4-thiadiazole;

compounds each having a hydroxy group in addition to the mercapto group, such as glycerine di(mercaptoacetate), 1-hydroxy-4-mercaptocyclohexane, 2,4-dimercaptophenol, 2-mercaptohydroquinone, 4-mercaptophenol, 3,4-dimercapto-2-propanol, 1,3-dimercapto-2-propanol, 2,3-dimercapto-1-propanol, 1,2-dimercapto-1,3-butanediol, pentaerythritol tris(3-mercaptopropionate), pentaerythritol mono(3-mercaptopropionate), pentaerythritol bis(3-mercaptopropionate), pentaerythritol tris(thioglycolate), dipentaerythritol pentakis(3-mercaptopropionate), hydroxymethyl-tris(mercaptoethylthiomethyl)methane, 1-hydroxyethylthio-3-mercaptoethylthiobenzene;

compounds having a dithioacetal or dithioketal skeleton, such as 1,1,3,3-tetrakis(mercaptomethylthio)propane, 1,1,2,2-tetrakis(mercaptomethylthio)ethane, 4,6-bis(mercaptomethylthio)-1,3-dithiacyclohexane, 1,1,5,5-tetrakis(mercaptomethylthio)-3-thiapentane, 1,1,6,6-tetrakis(mercaptomethylthio)-3,4-dithiahexane, 2,2-bis(mercaptomethylthio)ethanethiol, 2-(4,5-dimercapto-2-thiapentyl)-1,3-dithiacyclopentane, 2,2-bis(mercaptomethyl)-1,3-dithiacyclopentane, 2,5-bis(4,4-bis(mercaptomethylthio)-2-thiabutyl)-1,4-dithiane, 2,2-bis(mercaptomethylthio)-1,3-propanedithiol, 3-mercaptomethylthio-1,7-dimercapto-2,6-dithiaheptane, 3,6-bis(mercaptomethylthio)-1,9-dimercapto-2,5,8-trithianonane, 4,6-bis(mercaptomethylthio)-1,9-dimercapto-2,5,8-trithianonane, 3-mercaptomethylthio-1,6-dimercapto-2,5-dithiahexane, 2-(2,2-bis(mercaptomethylthio)ethyl)-1,3-dithietane, 1,1,9,9-tetrakis(mercaptomethylthio)-5-(3,3-bis(mercaptomethylthio)-1-thiapropyl)3,7-dithianonane, tris(2,2-bis(mercaptomethylthio)ethyl)methane, tris(4,4-bis(mercaptomethylthio)-2-thiabutyl)methane, tetrakis(2,2-bis(mercaptomethylthio)ethyl)methane, tetrakis(4,4-bis(mercaptomethylthio)-2-thiabutyl)methane, 3,5,9,11-tetrakis(mercaptomethylthio)-1,13-dimercapto-2,6,8,12-tetrathiamidecane, 3,5,9,11,15,17-hexakis(mercaptomethylthio)-1,19-dimercapto-2,6,8,12,14,18-hexathianonadecane, 9-(2,2-bis(mercaptomethylthio)ethyl)-3,5,13,15-tetrakis(mercaptomethylthio)-1,17-dimercapto-2,6,8,10,12,16-hexathiaheptadecane, 3,4,8,9-tetrakis(mercaptomethylthio)-1,11-dimercapto-2,5,7,10-tetrathiaundecane, 3,4,8,9,13,14-hexakis(mercaptomethylthio)-1,16-dimercapto-2,5,7,10,12,15-hexathiahexadecane, 8-{bis(mercaptomethylthio)methyl}-3,4,12,13-tetrakis(mercaptomethylthio)-1,15-dimercapto-2,5,7,9,11,14-hexathiapentadecane, 4,6-bis{3,5-bis(mercaptomethylthio)-7-mercapto-2,6-dithiaheptylthio}-1,3-dithiane, 4-{3,5-bis(mercaptomethylthio)-7-mercapto-2,6-dithiaheptylthio}-6-mercaptomethylthio-1,3-dithiane, 1,1-bis{4-(6-mercaptomethylthio)-1,3-dithianylthio}-3,3-bis(mercaptomethylthio)propane, 1,3-bis{4-(6-mercaptomethylthio)-1,3-dithianylthio}-1,3-bis(mercaptomethylthio)propane, 1-{4-(6-mercaptomethylthio)-1,3-dithianylthio}-3-{2,2-bis(mercaptomethylthio)ethyl}-7,9-bis(mercaptomethylthio)-2,4,6,10-tetrathiaundecane, 1-{4-(6-mercaptomethylthio)-1,3-dithianylthio}-3-{2-(1,3-dithietanyl)}methyl-7,9-bis(mercaptomethylthio)-2,4,6,10-tetrathiaundecane, 1,5-bis{4-(6-mercaptomethylthio)-1,3-dithianylthio}-3-{2-(1,3-dithietanyl)}methyl-2,4-dithiapentane, 4,6-bis[3-{2-(1,3-dithietanyl)}methyl-5-mercapto-2,4-dithiapentylthio]-1,3-dithiane, 4,6-bis{4-(6-mercaptomethylthio)-1,3-dithianylthio}-1,3-dithiane, 4-{4-(6-mercaptomethylthio)-1,3-dithianylthio}-6-{4-(6-mercaptomethylthio)-1,3-dithianylthio}-1,3-dithiane, 3-{2-(1,3-dithietanyl)}methyl-7,9-bis(mercaptomethylthio)-1,11-dimercapto-2,4,6,10-tetrathiaundecane, 9-{2-(1,3-dithietanyl)}methyl-3,5,13,15-tetrakis(mercaptomethylthio)-1,17-dimercapto-2,6,8,10,12,16-hexathiaheptadecane, 3-{2-(1,3-dithietanyl)}methyl-7,9,13,15-tetrakis(mercaptomethylthio)-1,17-dimercapto-2,4,6,10,12,16-hexathiaheptadecane, 3,7-bis{2-(1,3-dithietanyl)}methyl-1,9-dimercapto-2,4,6,8-tetrathianonane, 4-{3,4,8,9-tetrakis(mercaptomethylthio)-11-mercapto-2,5,7,10-tetrathiaundecyl}-5-mercaptomethylthio-1,3-dithiolane, 4,5-bis{3,4-bis(mercaptomethylthio)-6-mercapto-2,5-dithiahexylthio}-1,3-dithiolane, 4-{3,4-bis(mercaptomethylthio)-6-mercapto-2,5-dithiahexylthio}-5-mercaptomethylthio-1,3-dithiolane, 4-{3-bis(mercaptomethylthio)methyl-5,6-bis(mercaptomethylthio)-8-mercapto-2,4,7-trithiaoctyl}-5-mercaptomethylthio-1,3-dithiolane, 2-[bis{3, 4-bis(mercaptomethylthio)-6-mercapto-2,5-dithiahexylthio}methyl]-1,3-dithietane, 2-{3,4-bis(mercaptomethylthio)-6-mercapto-2,5-dithiahexylthio}mercaptomethylthiomethyl-1,3-dithietane, 2-{3,4,8,9-tetrakis(mercaptomethylthio)-11-mercapto-2,5,7,10-tetrathiaundecylthio}mercaptomethylthiomethyl-1,3-dithietane, 2-{3-bis(mercaptomethylthio)methyl-5,6-bis(mercaptomethylthio)-8-mercapto-2,4,7-trithiaoctyl}mercaptomethylthiomethyl-1,3-dithietane, 4,5-bis[1-{2-(1,3-dithietanyl)}-3-mercapto-2-thiapropylthio]-1,3-dithiolane, 4-[1-{2-(1,3-dithietanyl)}-3-mercapto-2-thiapropylthio]-5-{1,2-bis(mercaptomethylthio)-4-mercapto-3-thiabutylthio}-1,3-dithiolane, 2-[bis{4-(5-mercaptomethylthio-1,3-dithioranyl)thio}]methyl-1,3-dithietane, 4-{4-(5-mercaptomethylthio-1,3-dithioranyl)thio}-5-[1-{2-(1,3-dithietanyl)}-3-mercapto-2-thiapropylthio]-1,3-dithiolane, and their oligomers;

compounds having trithioorthoformamte ester skeleton, such as tris(mercaptomethylthio)methane, tris(mercaptoethylthio)methane, 1,1,5,5-tetrakis(mercaptomethylthio)-2,4-dithiapentane, bis[4,4-bis(mercaptomethylthio)-1,3-dithiabutyl](mercaptomethylthio)methane, tris[4,4-bis(mercaptomethylthio)-1,3-dithiabutyl]methane, 2,4,6-tris(mercaptomethylthio)-1,3,5-trithiacyclohexane, 2,4-bis(mercaptomethylthio)-1,3,5-trithiacyclohexane, 1,1,3,3-tetrakis(mercaptomethylthio)-2-thiapropane, bis(mercaptomethyl)methylthio-1,3,5-trithiacyclohexane, tris[(4-mercaptomethyl-2,5-dithiacyclohexyl-1-yl)methylthio]methane, 2,4-bis(mercaptomethylthio)-1,3-dithiacyclopentane, 2-mercaptoethylthio-4-mercaptomethyl-1,3-dithiacyclopentane, 2-(2,3-dimercaptopropylthio)-1,3-dithiacyclopentane, 4-mercaptomethyl-2-(2,3-dimercaptopropylthio)-1,3-dithiacyclopentane, 4-mercaptomethyl-2-(1,3-dimercapto-2-propylthio)-1,3-dithiacyclopentane, tris[2,2-bis(mercaptomethylthio)-1-thiaethyl]methane, tris[3,3-bis(mercaptomethylthio)-2-thiapropyl]methane, tris[4,4-bis(mercaptomethylthio)-3-thiabutyl]methane, 2,4,6-tris[3,3-bis(mercaptomethylthio)-2-thiapropyl]-1,3,5-trithiacyclohexane, tetrakis[3,3-bis(mercaptomethylthio)-2-thiapropyl]methane and their oligomers; and compounds each having tetrathioorthocarbonate ester skeleton, such as 3,3'-di(mercaptomethylthio)-1,5-dimercapto-2,4-dithiapentane, 2,2'-di(mercaptomethylthio)-1,3-dithiacyclopentane, 2,7-di(mercaptomethyl)-1,4,5,9-tetrathiaspiro[4,4] nonane, 3,9-dimercapto-1,5,7,11-tetrathiaspiro[5,5]undecane, and their oligomers and the like, but not limited to these exemplified compounds alone. These exemplified compounds may be used singly or in a mixture of two or more kinds thereof.

Among these thiol compounds, in consideration of the optical properties, particularly the Abbe number, of the obtained resin, it is preferable to select an aliphatic thiol compound rather than an aromatic thiol compound. Furthermore, in consideration of requirements of optical properties, particularly refractive index, it is much more preferable to select a compound having a sulfur group in addition to the thiol group such as a sulfide bond and/or a disulfide bond. From the viewpoint of enhancement of 3-dimensional crosslinkability considering the heat resistance of the obtained resin, it is particularly preferable to select one or more thiol compounds having a polymerizable group such as an epithio group, a thietanyl group or the like, or one or more compounds having three or more thiol groups.

Examples of the thiol which is preferable from the above viewpoint include 3-mercaptothiethane, 1-mercapto-2,3-epithiopropane, 1-mercaptomethylthio-2,3-epithiopropane, 1-mercaptoethyl thio-2,3-epithiopropane, 2-mercaptothiethane, 3-mercaptomethylthiothiethane, 2-mercaptomethylthiothiethane, 3-mercaptoethylthiothiethane, 2-mercaptoethylthiothiethane, 2,5-bis(mercaptomethyl)-1,4-dithiane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1,1-tetrakis(mercaptomethyl)methane, 1,1,3,3-tetrakis(mercaptomethylthio)propane, 1,1,2,2-tetrakis(mercaptomethylthio)ethane, 4,6-bis(mercaptomethylthio)-1,3-dithiane, and 2-(2,2-bis(mercaptomethylthio)ethyl)-1,3-dithietane.

More preferably, examples thereof include 3-mercaptothietane, 4-mercaptomethyl-1,8-dimercapto-3,6-dithiaoctane, 2,5-bis(mercaptomethyl)-1,4-dithiane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1,1-tetrakis(mercaptomethyl) methane, 1,1,3,3-tetrakis(mercaptomethylthio)propane, 1,1,2,2-tetrakis(mercaptomethylthio)ethane, 4,6-bis(mercaptomethylthio)-1,3-dithiane, and 2-(2,2-bis(mercaptomethylthio)ethyl)-1,3-dithietane. Further, when a divalent thiol compound is selected, it is preferable that a thiol compound having a polymerizable group and/or a tri- or higher valent thiol compound are mixed together and used.

More specifically, the thiol compound contains at least one selected from the group consisting of 3-mercaptothietane, 1,2-ethanedithiol, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 1,1,3,3-tetrakis(mercaptomethylthio)propane, 4,6-bis(mercaptomethylthio)-1,3-dithiane, 2-(2,2-bis(mercaptomethylthio)ethyl)-1,3-dithietane, and 2,5-bis(mercaptomethyl)-1,4-dithiane.

For the additive for a polymerizable composition of the present invention, by the combined use of this thiol compound, a resin having a high refractive index and excellent transparency and heat resistance can be obtained.

The amount of the thiol compound to be added is not particularly limited as long as it is in the range allowing dissolution of the additive, and an amount thereof may be added depending on a desired physical property (refractive index). In addition, when the additive of the present invention is dissolved in the thiol compound, the solubility can be improved by adding amines such as N,N-dicyclohexylmethylamine, triethylamine.

Since the additive of the present invention has excellent compatibility with a thiol compound, it is easily dissolved in the thiol compound. As such, even the additive of the present invention is contained in a lens having a high film thickness at the above amount, excellent transparency can be attained. That is, by using the additive of the present invention and the thiol compound in the above-described ranges, excellent transparency and improvement of a refractive index can be simultaneously accomplished.

Further, the additive of the present invention can be added to an upper limit of the solubility in the polymerizable compound as described later, but the addition amount can be suitably adjusted, taking the solubility of the additive of the present invention in the polymerizable compound, a preferred refractive index of the obtained resin, or other physical properties into consideration.

The content of the additive in the polymerizable composition of the present invention is, for example, from 1% by weight to 50% by weight, and preferably from 10% by weight to 40% by weight, from the viewpoint of obtaining a high refractive index resin.

(Polymerizable Compound)

As the polymerizable compound, at least one is selected from the group consisting of an isocyanate compound, an episulfide compound, an epoxy compound, and a thietane compound.

Examples of the isocyanate compound include the compounds containing one or more iso(thio)cyanate groups (NCO groups and/or NCS groups).

Specific examples of the isocyanate compound include aliphatic polyisocyanate compounds such as hexamethylene diisocyanate, 2,2-dimethylpentane diisocyanate, 2,2,4-trimethylhexane diisocyanate, butene diisocyanate, 1,3-butadiene-1,4-diisocyanate, 2,4,4-trimethylhexamethylene diisocyanate, 1,6,11-undecatriisocyanate, 1,3,6-hexamethylenetriisocyanate, 1,8-diisocyanato 4-isocyanatomethyloctane, bis(isocyanatoethyl) carbonate, bis(isocyanatoethyl)ether, lisine diisocyanatomethylester, lisine triisocyanate, m-xylylene diisocyanate, p-xylene diisocyanate, bis(isocyanatoethyl)benzene, bis(isocyanatopropyl)benzene, α,α,α',α'-tetramethyl xylene diisocyanate, bis(isocyanatobutyl)benzene, bis(isocyanatomethyl)naphthalene, bis(isocyanatomethyl)diphenyl ether, bis(isocyanatoethyl)phthalate, mesitylene triisocyanate, 2,6-di(isocyanatomethyl)furan;

alicyclic polyisocyanate compounds such as isophorone diisocyanate, bis(isocyanatomethyl)cyclohexane, dicyclohexyl methane diisocyanate, cyclohexane diisocyanate, methyl cyclohexane diisocyanate, dicyclohexyl dimethyl methane diisocyanate, 2,2-dimethyl dicyclohexyl methane diisocyanate, 2,5-bis(isocyanatomethyl)bicyclo[2,2,1]-heptane, 2,6-bis(isocyanatomethyl)bicyclo[2,2,1]-heptane, 3,8-bis(isocyanatomethyl)tricyclodecane, 3,9-bis(isocyanatomethyl)tricyclodecane, 4,8-bis(isocyanatomethyl)tricyclodecane, 4,9-bis (isocyanatomethyl)tricyclodecane, 1,1'-methylenebis(4-isocyanatocyclohexane);

aromatic polyisocyanate compounds such as phenylene diisocyanate, tolylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzenetriisocyanate, benzenetriisocyanate, biphenyldiisocyanate, toluidine diisocyanate, 4,4-diphenyl methane diisocyanate, 3,3-dimethyl diphenyl methane-4,4-diisocyanate, bibenzyl-4,4-diisocyanate, bis(isocyanatophenyl)ethylene, 3,3-dimethoxybiphenyl-4,4-diisocyanate, phenylisocyanatoethylisocyanate, hexahydrobenzene diisocyanate, hexahydrodiphenyl methane-4,4-diisocyanate;

sulfur-containing aliphatic polyisocyanate compounds such as bis(isocyanatomethyl)sulfide, bis(isocyanatoethyl)sulfide, bis(isocyanatopropyl)sulfide, bis(isocyanatohexyl)sulfide, bis(isocyanatomethyl)sulfone, bis(isocyanatomethyl)disulfide, bis(isocyanatoethyl)disulfide, bis(isocyanatopropyl)disulfide, bis(isocyanatomethylthio)methane, bis(isocyanatoethylthio)methane, bis(isocyanatoethylthio)ethane, bis(isocyanatomethylthio)ethane, 1,5-diisocyanato-2-isocyanatomethyl-3-thiapentane;

aromatic sulfide-based polyisocyanate compounds such as diphenyl sulfide-2,4-diisocyanate, diphenyl sulfide-4,4-diisocyanate, 3,3-dimethoxy-4,4-diisocyanatodibenzylthioether, bis(4-isocyanatomethylbenzene)sulfide, 4,4-methoxybenzene thioethyleneglycol-3,3-diisocyanate;

aromatic disulfide-based isocyanate compounds such as diphenyl disulfide-4,4-diisocyanate, 2,2-dimethyldiphenyl disulfide-5,5-diisocyanate, 3,3-dimethyldiphenyl disulfide-5,5-diisocyanate, 3,3-dimethyldiphenyl disulfide 6,6-diisocyanate, 4,4-dimethyldiphenyl disulfide-5,5-diisocyanate, 3,3-dimethoxydiphenyl disulfide-4,4-diisocyanate, 4,4-dimethoxydiphenyl disulfide 3,3-diisocyanate;

sulfur-containing heterocyclic polyisocyanate compounds such as 2,5-diisocyanatothiophene, 2,5-bis(isocyanatomethyl)thiophene; etc.

Other examples of the isocyanate compound include 2,5-diisocyanatotetrahydrothiophene, 2,5-bis(isocyanatomethyl)tetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, 4,5-bis(isocyanatomethyl)-1,3-dithiolane, 4,5-bis(isocyanatomethyl)-2-methyl-1,3-dithiolane, but not limited to these exemplary compounds.

Further, a halogen substitute such as a chlorine substitute or a bromine substitute, an alkyl substitute, an alkoxy substitute, a nitro substitute, polyhydric alcohol prepolymer-type modified products, carbodiimide-modified products, urea-modified products, burette-modified products, or dimerization or trimerization reaction products, of those compounds, can also be used.

In addition, specific examples of the isothiocyanate compound include monofunctional isothiocyanate compounds (compounds containing one isothiocyanate group), such as methyl isothiocyanate, ethyl isothiocyanate, n-propylthioisocyanate, isopropyl isothiocyanate, n-butyl isothiocyanate, sec-butyl isothiocyanate, tert-butyl isothiocyanate, pentyl isothiocyanate, hexyl isothiocyanate, heptyl isothiocyanate, octyl isothiocyanate, decyl isothiocyanate, lauryl isothiocyanate, myristyl isothiocyanate, octadecyl isothiocyanate, 3-pentyl isothiocyanate, 2-ethylhexyl isothiocyanate, 2,3-dimethylcyclohexyl isothiocyanate, 2-methoxyphenyl isothiocyanate, 4-methoxyphenyl isothiocyanate, α-methylbenzyl isothiocyanate, phenylethyl isothiocyanate, phenyl isothiocyanate, o-, m-, or p-tolyl isothiocyanate, cyclohexyl isothiocyanate, benzyl isothiocyanate, isothiocyanatemethylbicycloheptane;

aliphatic polyisothiocyanate compounds such as 1,6-diisothiocyanatohexane, p-phenyleneisopropylidenediisothiocyanate;

alicyclic polyisothiocyanate compounds such as cyclohexanediisothiocyanate, diisothiocyanatomethylbicycloheptane;

aromatic polyisothiocyanate compounds such as 1,2-diisothiocyanatobenzene, 1,3-diisothiocyanatobenzene, 1,4-diisothiocyanatobenzene, 2,4-diisothiocyanatotoluene, 2,5-diisothiocyanato-m-xylylene, 4,4-diisothiocyanato-1,1-biphenyl, 1,1-methylenebis(4-isothiocyanatobenzene), 1,1-methylenebis(4-isothiocyanato 2-methylbenzene), 1,1-methylenebis(4-isothiocyanato-3-methylbenzene), 1,1-(1,2-ethanediyl)bis(isothiocyanatobenzene), 4,4-diisothiocyanatobenzophenone, 4,4-diisothiocyanato-3,3-dimethylbenzophenone, diphenyl ether-4,4-diisothiocyanate, diphenylamine-4,4-diisothiocyanate;

carbonyl polyisothiocyanate compounds such as 1,3-benzenedicarbonyl diisothiocyanate, 1,4-benzenedicarbonyldiisothiocyanate, (2,2-pyridine)-4,4-dicarbonyldiisothiocyanate; etc., but not limited to these exemplary compounds.

Furthermore, specific examples of the isothiocyanate compound having one or more sulfur atoms in addition to an isothiocyanato group include sulfur-containing aliphatic polyisothiocyanate compounds such as thiobis(3-isothiocyanatopropane), thiobis(2-isothiocyanatoethane), dithiobis(2-isothiocyanatoethane);

sulfur-containing aromatic polyisothiocyanate compounds such as 1-isothiocyanato-4-[(2-isothiocyanato)sulfonyl]benzene, thiobis(4-isothiocyanatobenzene), sulfonylbis(4-isothiocyanatobenzene), dithiobis(4-isothiocyanatobenzene);

sulfur-containing heterocyclic polyisothiocyanate compounds such as 2,5-diisothiocyanatothiophene, 2,5-diisothiocyanato-1,4-dithiane; etc., but not limited to these exemplary compounds.

Further, a halogen substitute such as a chlorine substitute or a bromine substitute, an alkyl substitute, an alkoxy substitute, a nitro substitute, polyhydric alcohol prepolymer-type modified products, carbodiimide-modified products, urea-modified products, burette-modified products, or dimerization or trimerization reaction products, of those compounds, can also be used.

In addition, isothiocyanate compounds having isocyanate groups may be included. Specific examples thereof include aliphatic or alicyclic compounds such as 1-isocyanato-6-isothiocyanatohexane, 1-isocyanato-4-isothiocyanatocyclohexane;

aromatic compounds such as 1-isocyanato-4-isothiocyanatobenzene, 4-methyl-3-isocyanato-1-isothiocyanatobenzene;

heterocyclic compounds such as 2-isocyanato-4,6-diisothiocyanato-1,3,5-triazine;

compounds each containing a sulfur atom in addition to an isothiocyanato group, such as 4-isocyanato-4'-isothiocyanatodiphenyl sulfide, 2-isocyanato-2'-isothiocyanatodiethyl disulfide; etc., but not limited to these exemplary compounds.

Further, a halogen substituent such as a chlorine substituent or a bromine substituent, an alkyl substituent, an alkoxy substituent, a nitro substituent, polyhydric alcohol prepolymer-type modified products, carbodiimide-modified products, urea-modified products, burette-modified products, or dimerization or trimerization reaction products, of those compounds, can also be used.

Among these compounds, the most preferable compound is at least one selected from the group consisting of 2,5-bis(isocyanatomethyl)bicyclo[2.2.1]heptane, 2,6-bis(isocyanatomethyl)bicyclo[2.2.1]heptane, bis(isocyanatomethyl)cyclohexane, cyclohexane diisocyanate, isophorone diisocyanate, 1,1'-methylenebis(4-isocyanatocyclohexane), m-xylylene diisocyanate, and 2,5-bis(isocyanatomethyl)-1,4-dithiane, and the further preferable compounds are 2,5-bis(isocyanatomethyl)bicyclo[2.2.1]heptane, and 2,6-bis(isocyanatomethyl)bicyclo[2.2.1]heptane.

Specific examples of the episulfide compound (epithio compound) include epithioethylthio compounds such as bis(1,2-epithioethyl)sulfide, bis(1,2-epithioethyl)disulfide, bis(epithioethylthio)methane, bis(epithioethylthio)benzene, bis[4-(epithioethylthio)phenyl]sulfide, bis[4-(epithioethylthio)phenyl]methane;

chained aliphatic 2,3-epithiopropylthio compounds such as bis(2,3-epithiopropyl)sulfide, bis(2,3-epithiopropyl)disulfide, bis(2,3-epithiopropylthio)methane, 1,2-bis(2,3-epithiopropylthio)ethane, 1,2-bis(2,3-epithiopropylthio)propane, 1,3-bis(2,3-epithiopropylthio)propane, 1,3-bis(2,3-epithiopropylthio)-2-methylpropane, 1,4-bis(2,3-epithiopropylthio)butane, 1,4-bis(2,3-epithiopropylthio)-2-methylbutane, 1,3-bis(2,3-epithiopropylthio)butane, 1,5-bis(2,3-epithiopropylthio)pentane, 1,5-bis(2,3-epithiopropylthio)-2-methylpentane, 1,5-bis(2,3-epithiopropylthio)-3-thiapentane, 1,6-bis(2,3-epithiopropylthio)hexane, 1,6-bis(2,3-epithiopropylthio)-2-methylhexane, 3,8-bis(2,3-epithiopropylthio)-3,6-dithiaoctane, 1,2,3-tris(2,3-epithiopropylthio)propane, 2,2-bis(2,3-epithiopropylthio)-1,3-bis(2,3-epithiopropylthiomethyl)propane, 2,2-bis(2,3-epithiopropylthiomethyl)-1-(2,3-epithiopropylthio)butane, 1,5-bis(2,3-epithiopropylthio)-2-(2,3-epithiopropylthiomethyl)-3-thiapentane, 1,5-bis(2,3-epithiopropylthio)-2,4-bis(2,3-epithiopropylthiomethyl)-3-thiapentane, 1-(2,3-epithiopropylthio)-2,2-bis(2,3-epithiopropylthiomethyl)-4-thiahexane, 1,5,6-tris(2,3-epithiopropylthio)-4-(2,3-epithiopropylthiomethyl)-3-thiahexane, 1,8-bis(2,3-epithiopropylthio)-4-(2,3-epithiopropylthiomethyl)-3,6-dithiaoctane, 1,8-bis(2,3-epithiopropylthio)-4,5-bis(2,3-epithiopropylthiomethyl)-3,6-dithiaoctane, 1,8-bis(2,3-epithiopropylthio)-4,4-bis(2,3-epithiopropylthiomethyl)-3,6-dithiaoctane, 1,8-bis(2,3-epithiopropylthio)-2,5-bis(2,3-epithiopropylthiomethyl)-3,6-dithiaoctane, 1,8-bis(2,3-epithiopropylthio)-2,4,5-tris(2,3-epithiopropylthiomethyl)-3,6-dithiaoctane, 1,1,1-tris[[2-(2,3-epithiopropylthio)ethyl]thiomethyl]-2-(2,3-epithiopropylthio)ethane, 1,1,2,2-tetrakis[[2-(2,3-epithiopropylthio)ethyl]thiomethyl]ethane, 1,11-bis(2,3-epithiopropylthio)-4,8-bis(2,3-epithiopropylthiomethyl)-3,6,9-trithiaundecane, 1,11-bis(2,3-epithiopropylthio)-4,7-bis(2,3-epithiopropylthiomethyl)-3,6,9-trithiaundecane, 1,11-bis(2,3-epithiopropylthio)-5,7-bis(2,3-epithiopropylthiomethyl)-3,6,9-trithiaundecane;

cyclic aliphatic 2,3-epithiopropylthio compounds such as 1,3-bis(2,3-epithiopropylthio)cyclohexane, 1,4-bis(2,3-epithiopropylthio)cyclohexane, 1,3-bis(2,3-epithiopropylthiomethyl)cyclohexane, 1,4-bis(2,3-epithiopropylthiomethyl)cyclohexane, 2,5-bis(2,3-epithiopropylthiomethyl)-1,4-dithiane, 2,5-bis[[2-(2,3-epithiopropylthio)ethyl]thiomethyl]-1,4-dithiane, 2,5-bis(2,3-epithiopropylthiomethyl)-2,5-dimethyl-1,4-dithiane;

aromatic 2,3-epithiopropylthio compounds such as 1,2-bis(2,3-epithiopropylthio)benzene, 1,3-bis(2,3-epithiopropylthio)benzene, 1,4-bis(2,3-epithiopropylthio)benzene, 1,2-bis(2,3-epithiopropylthiomethyl)benzene, 1,3-bis(2,3-epithiopropylthiomethyl)benzene, 1,4-bis(2,3-epithiopropylthiomethyl)benzene, bis[4-(2,3-epithiopropylthio)phenyl]methane, 2,2-bis[4-(2,3-epithiopropylthio)phenyl]propane, bis[4-(2,3-epithiopropylthio)phenyl]sulfide, bis[4-(2,3-epithiopropylthio)phenyl]sulfone, 4,4'-bis(2,3-epithiopropylthio)biphenyl;

monofunctional episulfide compounds (compounds having one episulfide group) such as ethylene sulfide, propylene sulfide, mercaptopropylene sulfide, mercaptobutene sulfide, epithiochlorohydrin;

chained aliphatic 2,3-epithiopropyloxy compounds such as bis(2,3-epithiopropyl)ether, bis(2,3-epithiopropyloxy)methane, 1,2-bis(2,3-epithiopropyloxy)ethane, 1,2-bis(2,3-epithiopropyloxy)propane, 1,3-bis(2,3-epithiopropyloxy)propane, 1,3-bis(2,3-epithiopropyloxy)-2-methylpropane, 1,4-bis(2,3-epithiopropyloxy)butane, 1,4-bis(2,3-epithiopropyloxy)-2-methylbutane, 1,3-bis(2,3-epithiopropyloxy)butane, 1,5-bis(2,3-epithiopropyloxy)pentane, 1,5-bis(2,3-epithiopropyloxy)-2-methylpentane, 1,5-bis(2,3-epithiopropyloxy)-3-thiapentane, 1,6-bis(2,3-epithiopropyloxy)hexane, 1,6-bis(2,3-epithiopropyloxy)-2-methylhexane, 3,8-bis(2,3-epithiopropyloxy)-3,6-dithiaoctane, 1,2,3-tris(2,3-epithiopropyloxy)propane, 2,2-bis(2,3-epithiopropyloxy)-1,3-bis(2,3-epithiopropyloxymethyl)propane, 2,2-bis(2,3-epithiopropyloxymethyl)-1-(2,3-epithiopropyloxy)butane, 1,5-bis(2,3-epithiopropyloxy)-2-(2,3-epithiopropyloxymethyl)-3-thiapentane, 1,5-bis(2,3-epithiopropyloxy)-2,4-bis (2,3-epithiopropyloxymethyl)-3-thiapentane, 1-(2,3-epithiopropyloxy)-2,2-bis(2,3-epithiopropyloxymethyl)-4-thiahexane, 1,5,6-tris(2,3-epithiopropyloxy)-4-(2,3-epithiopropyloxymethyl)-3-thiahexane, 1,8-bis(2,3-epithiopropyloxy)-4-(2,3-epithiopropyloxymethyl)-3,6-dithiaoctane, 1,8-bis(2,3-epithiopropyloxy)-4,5-bis(2,3-epithiopropyloxymethyl)-3,6-dithiaoctane, 1,8-bis(2,3-epithiopropyloxy)-4,4-bis(2,3-epithiopropyloxymethyl)-3,6-dithiaoctane, 1,8-bis(2,3-epithiopropyloxy)-2,5-bis(2,3-epithiopropyloxymethyl)-3,6-dithiaoctane, 1,8-bis(2,3-epithiopropyloxy)-2,4,5-tris(2,3-epithiopropyloxymethyl)-3,6-dithiaoctane, 1,1,1-tris[[2-(2,3-epithiopropyloxy)ethyl]thiomethyl]-2-(2,3-epithiopropyloxy)ethane, 1,1,2,2-tetrakis[[2-(2,3-epithiopropyloxy)ethyl]thiomethyl]ethane, 1,11-bis(2,3-epithiopropyloxy)-4,8-bis(2,3-epithiopropyloxymethyl)-3,6,9-trithiaundecane, 1,11-bis(2,3-epithiopropyloxy)-4,7-bis(2,3-epithiopropyloxymethyl)-3,6,9-trithiaundecane, 1,11-bis(2,3-epithiopropyloxy)-5,7-bis(2,3-epithiopropyloxymethyl)-3,6,9-trithiaundecane;

cyclic aliphatic 2,3-epithiopropyloxy compounds such as 1,3-bis(2,3-epithiopropyloxy)cyclohexane, 1,4-bis(2,3-epithiopropyloxy)cyclohexane, 1,3-bis(2,3-epithiopropyloxymethyl)cyclohexane, 1,4-bis(2,3-epithiopropyloxymethyl)cyclohexane, 2,5-bis(2,3-epithiopropyloxymethyl)-1,4-dithiane, 2,5-bis[[2-(2,3-epithiopropyloxy)ethyl]thiomethyl]-1,4-dithiane, 2,5-bis(2,3-epithiopropyloxymethyl)-2,5-dimethyl-1,4-dithiane;

aromatic 2,3-epithiopropyloxy compounds such as 1,2-bis(2,3-epithiopropyloxy)benzene, 1,3-bis(2,3-epithiopropyloxy)benzene, 1,4-bis(2,3-epithiopropyloxy)benzene, 1,2-bis(2,3-epithiopropyloxymethyl)benzene, 1,3-bis(2,3-epithiopropyloxymethyl)benzene, 1,4-bis(2,3-epithiopropyloxymethyl)benzene, bis[4-(2,3-epithiopropyloxy)phenyl]methane, 2,2-bis[4-(2,3-epithiopropyloxy)phenyl]propane, bis[4-(2,3-epithiopropyloxy)phenyl]sulfide, bis[4-(2,3-epithiopropyloxy)phenyl]sulfone, 4,4'-bis(2,3-epithiopropyloxy)biphenyl; etc., but not limited to these exemplified compounds.

Of these exemplified compounds, preferable compounds are bis(1,2-epithioethyl)sulfide, bis(1,2-epithioethyl)disulfide, bis(2,3-epithiopropyl)sulfide, bis(2,3-epithiopropylthio)methane, and bis(2,3-epithiopropyl)disulfide, and more preferable compounds are bis(1,2-epithioethyl)sulfide, bis(1,2-epithioethyl)disulfide, bis(2,3-epithiopropyl)sulfide, and bis(2,3-epithiopropyl)disulfide. Further, even more preferable compounds are bis(2,3-epithiopropyl)sulfide and bis(2,3-epithiopropyl)disulfide.

Examples of the epoxy compound include phenol-based epoxy compounds obtained by a condensation reaction of an epihalohydrin compound with a polyvalent phenol compound such as bisphenol A glycidyl ether, bisphenol F glycidyl ether;

alcohol-based epoxy compounds each obtained by condensation of an epihalohydrin compound with a polyvalent alcohol compound such as hydrogenated bisphenol A glycidyl ether, hydrogenated bisphenol F glycidyl ether, cyclohexanedimethanol;

glycidyl ester-based epoxy compounds obtained by condensation of an epihalohydrin compound with a polyvalent organic acid compounds such as 3,4-epoxycyclohexylmethyl-3',4'-epoxycyclohexane carboxylate, 1,2-hexahydrophthalic acid diglycidyl ester;

amine-based epoxy compounds obtained by condensation of an epihalohydrin compound with primary and secondary amine compounds; and the like. In addition, other examples include aliphatic polyvalent epoxy compounds including vinylcyclohexene diepoxide such as 4-vinyl-1-cyclohexane diepoxide and the like; etc.

Specific examples of the sulfide group-containing epoxy compound and the ether group-containing epoxy compound include chained aliphatic 2,3-epoxypropylthio compounds such as bis(2,3-epoxypropyl)sulfide, bis(2,3-epoxypropyl)disulfide, bis(2,3-epoxypropylthio)methane, 1,2-bis(2,3-epoxypropylthio)ethane, 1,2-bis(2,3-epoxypropylthio)propane, 1,3-bis(2,3-epoxypropylthio)propane, 1,3-bis(2,3-epoxypropylthio)-2-methylpropane, 1,4-bis(2,3-epoxypropylthio)butane, 1,4-bis(2,3-epoxypropylthio)-2-methylbutane, 1,3-bis(2,3-epoxypropylthio)butane, 1,5-bis(2,3-epoxypropylthio)pentane, 1,5-bis(2,3-epoxypropylthio)-2-methylpentane, 1,5-bis(2,3-epoxypropylthio)-3-thiapentane, 1,6-bis(2,3-epoxypropylthio)hexane, 1,6-bis(2,3-epoxypropylthio)-2-methylhexane, 3,8-bis(2,3-epoxypropylthio)-3,6-dithiaoctane, 1,2,3-tris(2,3-epoxypropylthio)propane, 2,2-bis(2,3-epoxypropylthio)-1,3-bis(2,3-epoxypropylthiomethyl)propane, 2,2-bis(2,3-epoxypropylthiomethyl)-1-(2,3-epoxypropylthio)butane, 1,5-bis(2,3-epoxypropylthio)-2-(2,3-epoxypropylthiomethyl)-3-thiapentane, 1,5-bis(2,3-epoxypropylthio)-2,4-bis(2,3-epoxypropylthiomethyl)-3-thiapentane, 1-(2,3-epoxypropylthio)-2,2-bis(2,3-epoxypropylthiomethyl)-4-thiahexane, 1,5,6-tris(2,3-epoxypropylthio)-4-(2,3-epoxypropylthiomethyl)-3-thiahexane, 1,8-bis(2,3-epoxypropylthio)-4-(2,3-epoxypropylthiomethyl)-3,6-dithiaoctane, 1,8-bis(2,3-epoxypropylthio)-4,5-bis(2,3-epoxypropylthiomethyl)-3,6-dithiaoctane, 1,8-bis(2,3-epoxypropylthio)-4,4-bis(2,3-epoxypropylthiomethyl)-3,6-dithiaoctane, 1,8-bis(2,3-epoxypropylthio)-2,5-bis(2,3-epoxypropylthiomethyl)-3,6-dithiaoctane, 1,8-bis(2,3-epoxypropylthio)-2,4,5-tris(2,3-epoxypropylthiomethyl)-3,6-dithiaoctane, 1,1,1-tris[[2-(2,3-epoxypropylthio)ethyl]thiomethyl]-2-(2,3-epoxypropylthio)ethane, 1,1,2,2-tetrakis[[2-(2,3-epoxypropylthio)ethyl]thiomethyl]ethane, 1,11-bis(2,3-epoxypropylthio)-4,8-bis(2,3-epoxypropylthiomethyl)-3,6,9-trithiaundecane, 1,11-bis(2,3-epoxypropylthio)-4,7-bis(2,3-epoxypropylthiomethyl)-3,6,9-trithiaundecane, 1,11-bis(2,3-epoxypropylthio)-5,7-bis(2,3-epoxypropylthiomethyl)-3,6,9-trithiaundecane;

cyclic aliphatic 2,3-epoxypropylthio compounds such as 1,3-bis(2,3-epoxypropylthio)cyclohexane, 1,4-bis(2,3-epoxypropylthio)cyclohexane, 1,3-bis(2,3-epoxypropylthiomethyl)cyclohexane, 1,4-bis(2,3-epoxypropylthiomethyl)cyclohexane, 2,5-bis(2,3-epoxypropylthiomethyl)-1,4-dithiane, 2,5-bis[[2-(2,3-epoxypropylthio)ethyl]thiomethyl]-1,4-dithiane, 2,5-bis(2,3-epoxypropylthiomethyl)-2,5-dimethyl-1,4-dithiane;

aromatic 2,3-epoxypropylthio compounds such as 1,2-bis(2,3-epoxypropylthio)benzene, 1,3-bis(2,3-epoxypropylthio)benzene, 1,4-bis(2,3-epoxypropylthio)benzene; 1,2-bis(2,3-epoxypropylthiomethyl)benzene, 1,3-bis(2,3-epoxypropylthiomethyl)benzene, 1,4-bis(2,3-epoxypropylthiomethyl)benzene, bis[4-(2,3-epoxypropylthio)phenyl]methane, 2,2-bis[4-(2,3-epoxypropylthio)phenyl]propane, bis[4-(2,3-epoxypropylthio)phenyl]sulfide, bis[4-(2,3-epoxypropylthio)phenyl]sulfone, 4,4'-bis(2,3-epoxypropylthio)biphenyl;

monofunctional epoxy compounds (compounds having one epoxy groups) such as ethylene oxide, propylene oxide, glycidol, epichlorohydrin;

chained aliphatic 2,3-epoxypropyloxy compounds such as bis(2,3-epoxypropyl)ether, bis(2,3-epoxypropyloxy)methane, 1,2-bis(2,3-epoxypropyloxy)ethane, 1,2-bis(2,3-epoxypropyloxy)propane, 1,3-bis(2,3-epoxypropyloxy)propane, 1,3-bis(2,3-epoxypropyloxy)-2-methylpropane, 1,4-bis(2,3-epoxypropyloxy)butane, 1,4-bis(2,3-epoxypropyloxy)-2-methylbutane, 1,3-bis(2,3-epoxypropyloxy)butane, 1,5-bis(2,3-epoxypropyloxy)pentane, 1,5-bis(2,3-epoxypropyloxy)-2-methylpentane, 1,5-bis(2,3-epoxypropyloxy)-3-thiapentane, 1,6-bis(2,3-epoxypropyloxy)hexane, 1,6-bis(2,3-epoxypropyloxy)-2-methylhexane, 3,8-bis(2,3-epoxypropyloxy)-3,6-dithiaoctane, 1,2,3-tris(2,3-epoxypropyloxy)propane, 2,2-bis(2,3-epoxypropyloxy)-1,3-bis(2,3-epoxypropyloxymethyl)propane, 2,2-bis(2,3-epoxypropyloxymethyl)-1-(2,3-epoxypropyloxy)butane, 1,5-bis(2,3-epoxypropyloxy)-2-(2,3-epoxypropyloxymethyl)-3-thiapentane, 1,5-bis(2,3-epoxypropyloxy)-2,4-bis(2,3-epoxypropyloxymethyl)-3-thiapentane, 1-(2,3-epoxypropyloxy)-2,2-bis(2,3-epoxypropyloxymethyl)-4-thiahexane, 1,5,6-tris(2,3-epoxypropyloxy)-4-(2,3-epoxypropyloxymethyl)-3-thiahexane, 1,8-bis(2,3-epoxypropyloxy)-4-(2,3-epoxypropyloxymethyl)-3,6-dithiaoctane, 1,8-bis(2,3-epoxypropyloxy)-4,5-bis(2,3-epoxypropyloxymethyl)-3,6-dithiaoctane, 1,8-bis(2,3-epoxypropyloxy)-4,4-bis(2,3-epoxypropyloxymethyl)-3,6-dithiaoctane, 1,8-bis(2,3-epoxypropyloxy)-2,5-bis(2,3-epoxypropyloxymethyl)-3,6-dithiaoctane, 1,8-bis(2,3-epoxypropyloxy)-2,4,5-tris(2,3-epoxypropyloxymethyl)-3,6-dithiaoctane, 1,1,1-tris[[2-(2,3-epoxypropyloxy)ethyl]thiomethyl]-2-(2,3-epoxy propyloxy) ethane, 1,1,2,2-tetrakis[[2-(2,3-epoxypropyloxy)ethyl]thiomethyl]ethane, 1,11-bis(2,3-epoxypropyloxy)-4,8-bis(2,3-epoxypropyloxymethyl)-3,6,9-trithiaundecane, 1,11-bis(2,3-epoxypropyloxy)-4,7-bis(2,3-epoxypropyloxymethyl)-3,6,9-trithiaundecane, 1,11-bis(2,3-epoxypropyloxy)-5,7-bis(2,3-epoxypropyloxymethyl)-3,6,9-trithiaundecane;

cyclic aliphatic 2,3-epoxypropyloxy compounds such as 1,3-bis(2,3-epoxypropyloxy)cyclohexane, 1,4-bis(2,3-epoxypropyloxy)cyclohexane, 1,3-bis(2,3-epoxypropyloxymethyl)cyclohexane, 1,4-bis(2,3-epoxypropyloxymethyl)cyclohexane, 2,5-bis(2,3-epoxypropyloxymethyl)-1,4-dithiane, 2,5-bis[[2-(2,3-epoxypropyloxy)ethyl]thiomethyl]-1,4-dithiane, 2,5-bis(2,3-epoxypropyloxymethyl)-2,5-dimethyl-1,4-dithiane;

aromatic 2,3-epoxypropyloxy compounds such as 1,2-bis(2,3-epoxypropyloxy)benzene, 1,3-bis(2,3-epoxypropyloxy)benzene, 1,4-bis(2,3-epoxypropyloxy)benzene, 1,2-bis(2,3-epoxypropyloxymethyl)benzene, 1,3-bis(2,3-epoxypropyloxymethyl)benzene, 1,4-bis(2,3-epoxypropyloxymethyl)benzene, bis[4-(2,3-epoxypropyloxy)phenyl]methane, 2,2-bis[4-(2,3-epoxypropyloxy)phenyl]propane, bis[4-(2,3-epoxypropyloxy)phenyl]sulfide, bis[4-(2,3-epoxypropyloxy)phenyl]sulfone, 4,4'-bis(2,3-epoxypropyloxy)biphenyl; etc., but not limited to these exemplified compounds.

Among these exemplified epoxy compounds, preferable examples include phenol-based epoxy compounds obtained by a condensation reaction of an epihalohydrin compound with a polyvalent phenol compound such as bis(2,3-epoxypropyl)disulfide, 4-vinyl-1-cyclohexanediepoxide, bisphenol A glycidyl ether, bisphenol F glycidyl ether;

alcohol-based epoxy compounds obtained by condensation of an epihalohydrin compound with a polyvalent alcohol compound such as hydrogenated bisphenol A glycidyl ether, hydrogenated bisphenol F glycidyl ether;

glycidyl ester-based epoxy compounds obtained by condensation of an epihalohydrin compound with a polyvalent organic acid compounds such as 3,4-epoxycyclohexylmethyl-3',4'-epoxycyclohexane carboxylate, 1,2-hexahydrophthalic acid diglycidyl ester;

amine-based epoxy compounds obtained by condensation of an epihalohydrin compound with primary and secondary amine compounds; and the like. In addition, other examples include aliphatic polyvalent epoxy compounds including vinylcyclohexene diepoxide and the like, more preferably bis(2,3-epoxypropyl)disulfide, cyclohexane dimethanol diglycidyl ether, bisphenol A glycidyl ether, bisphenol F glycidyl ether, and further preferably cyclohexane dimethanol diglycidyl ether and bisphenol F glycidyl ether.

As the thietane compound, a metal-containing thietane compound or a non-metal thietane compound can be used. First, the metal-containing thietane compound will be described.

The metal-containing thietane compound is represented by the following general formula (7).

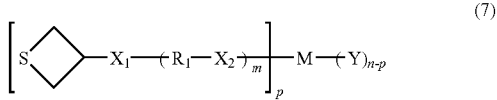

(In the general formula (7), M represents a metal atom, $X_1$ and $X_2$ each independently represent a sulfur atom or an oxygen atom, $R_1$ represents a divalent organic group, m represents an integer of 0 or 1 or more, p represents an integer of 1 to n, n represents a valence of a metal atom M, Y each independently represent an inorganic or organic residue, and when n-p is 2 or more, Y may be bonded to each other to form a ring containing a metal atom M).

First, M in the general formula (7) will be described. In the general formula (7), M represents a metal atom. Examples of M include:

a Group 11 element in a long form of the Periodic Table such as a Cu atom, an Au atom, and an Ag atom (the same will be applied in the below description);

a Group 12 element such as a Zn atom and the like;

a Group 13 element such as an Al atom and the like;

a Group 4 element such as a Zr atom, a Ti atom;

a Group 14 element such as a Sn atom, a Si atom, a Ge atom, a Pb atom;

a Group 15 element such as a Bi atom and the like; and a Group 8 or 10 element such as a Fe atom, a Pt atom.

M is preferably a Group 14 element such as a Sn atom, a Si atom, a Ge atom, a Pb atom;

a Group 4 element such as a Zr atom, a Ti atom;

a Group 13 element such as an Al atom and the like; or a Group 12 element such as a Zn atom and the like;

more preferably, a Group 14 element such as a Sn atom, a Si atom, a Ge atom; or a Group 4 element such as a Zr atom, a Ti atom;

and even more preferably, an Sn atom.

Next, the group containing a thietanyl group and bonding to M, in the general formula (7), will be described. In the general formula (7), $X_1$ and $X_2$ each independently represent a sulfur atom or an oxygen atom. In consideration of a high refractive index as a desired effect of the present invention, $X_1$ and $X_2$ are each more preferably a sulfur atom.

In the general formula (7), $R_1$ represents a divalent organic group.

Examples of such a divalent organic group include a chained or alicyclic group, an aromatic group or an aromatic-aliphatic group, preferably a chained aliphatic group having 1 to 20 carbon atom (s), an alicyclic group having 3 to 20 carbon atoms, an aromatic group having 5 to 20 carbon atoms and an aromatic-aliphatic group having 6 to 20 carbon atoms.

More specifically, as $R_1$, this divalent organic group is a chained or alicyclic group, an aromatic group or an aromatic-aliphatic group, preferably a substituted or unsubstituted chained or alicyclic group having 1 to 20 carbon atoms such as a methylene group, an ethylene group, a 1,2-dichloroethylene group, a trimethylene group, a tetramethylene group, a pentamethylene group, a cyclopentylene group, a hexamethylene group, a cyclohexylene group, a heptamethylene group, an octamethylene group, a nonamethylene group, a decamethylene group, an undecamethylene group, a dodecamethylene group, a tridecamethylene group, a tetradecamethylene group, a pentadecamethylene group;

a substituted or unsubstituted aromatic group having 5 to 20 carbon atoms, such as a phenylene group, a chlorophenylene group, a naphthylene group, an indenylene group, an anthracenylene group, a fluorenylene group; or a substituted or unsubstituted aromatic-aliphatic group having 6 to 20 carbon atoms such as a —$C_6H_4$—$CH_2$— group, a —$CH_2$—$C_6H_4$—$CH_2$— group, a —$CH_2$—$C_6H_3$(Cl)—$CH_2$— group, a —$C_{10}H_6$—$CH_2$— group, a —$CH_2$—$C_{10}H_6$—$CH_2$— group, a —$CH_2CH_2$—$C_6H_4$—$CH_2CH_2$— group.

$R_1$ is more preferably a substituted or unsubstituted chained or alicyclic group having 1 to 6 carbon atoms such as a methylene group, an ethylene group, a 1,2-dichloroethylene group, a trimethylene group, a cyclopentylene group, a cyclohexylene group;

a substituted or unsubstituted aromatic group having 5 to 15 carbon atoms such as a phenylene group, a chlorophenylene group, a naphthylene group, an indenylene group, an anthracenylene group, a fluorenylene group; or a substituted or unsubstituted aromatic-aliphatic group having 6 to 15 carbon atoms such as a —$C_6H_4$—$CH_2$— group, a —$CH_2$—$C_6H_4$—$CH_2$— group, a —$CH_2$—$C_6H_3$(Cl)—$CH_2$— group, a —$C_{10}H_6$—$CH_2$— group, a —$CH_2$—$C_{10}H_6$—$CH_2$— group, a —$CH_2CH_2$—$C_6H_4$—$CH_2CH_2$— group.

This divalent organic group may contain a heteroatom other than a carbon atom or a hydrogen atom in the group. Examples of the heteroatom include an oxygen atom or a sulfur atom. Considering the desired effect of the present invention, a sulfur atom is preferable.

In the general formula (7), m represents an integer of 0 or 1 or more. Examples of this m are preferably an integer from 0 to 4, more preferably an integer from 0 to 2, and still more preferably an integer of 0 or 1.

Furthermore, for the group containing a thietanyl group and bonding to M in the general formula (7), it is more preferable that m is 0 and $X_1$ is a sulfur atom. Here, the general formula (7) is represented by the following the general formula (8).

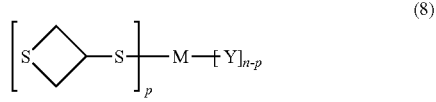

(8)

In the general formula (8), M, Y, p, and n are the same as M, Y, p, and n, respectively, in the general formula (7)).

Furthermore, in the general formula (8), preferably n is p, and more preferably n is p, and M is Sn.

Next, in the general formula (7) or (8), the —$(Y)_{n-p}$ group bonding to M will be described.

In the general formula (7) or (8), n represents a valence of a metal atom M.

Further, p represents an integer from 1 to n. This p is preferably n, n−1, or n−2, and more preferably n or n−1.

In the general formula (7) or (8), plural Y each independently represent an inorganic or organic residue.

If the compound represented by the general formula (7) or (8) contains a plurality of Y's, the plurality of Y's each independently represent an inorganic or organic residue. That is, the plurality of Y may be the same as or different from each other. More specifically, the plurality of Y may be different from each other, some of the plurality of Y may be the same as each other, or all of the plurality of Y may be the same.

Examples of the inorganic or organic residue that constitutes Y include, without any particular limitation, a hydrogen atom, a halogen atom, a hydroxyl group, a thiol group, a substituted or unsubstituted alkyl group, a substituted or unsubstituted aryl group, a substituted or unsubstituted aralkyl group, a substituted or unsubstituted alkoxy group, a substituted or unsubstituted alkylthio group, a substituted or unsubstituted aryloxy group, and a substituted or unsubstituted arylthio group.

Among these, the halogen atom, the substituted or unsubstituted alkyl group, the substituted or unsubstituted aryl group, the substituted or unsubstituted aralkyl group, the substituted or unsubstituted alkoxy(alkyloxy) group, the substituted or unsubstituted alkylthio group, the substituted or unsubstituted aryloxy group, and the substituted or unsubstituted arylthio group will be each described.

Specific examples of the halogen atom include a fluorine atom, a chlorine atom, a bromine atom, and an iodine atom.

Specific examples of the substituted or unsubstituted alkyl group include linear alkyl groups having 1 to 10 carbon atoms in total, such as a methyl group, an ethyl group, an n-propyl group, an n-butyl group, an n-pentyl group, an n-hexyl group;

branched alkyl groups having 3 to 10 carbon atoms in total, such as an isopropyl group, an isobutyl group, a sec-butyl group, an isopentyl group, a sec-pentyl group, a 1-methylpentyl group, a 2-methylpentyl group, a 3-methylpentyl group, a 4-methylpentyl group, a 1-ethylbutyl group, a 2-ethylbutyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 1-n-propylbutyl group, a 1-iso-propylbutyl group, a 1-iso-propyl-2-methylpropyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 3-ethylhexyl group, a 4-ethylhexyl group, a 1-n-propylpentyl group, a 2-n-propylpentyl group, a 1-iso-propylpentyl group, a 2-iso-propylpentyl group, a 1-n-butylbutyl group, a 1-iso-butylbutyl group, a 1-sec-butylbutyl group, a 1-tert-butylbutyl group, a 2-tert-butylbutyl group, a tert-butyl group, a tert-pentyl group, a 1,1-dimethylbutyl group, a 1,2-dimethylbutyl group, a 1,3-dimethylbutyl group, a 2,3-dimethylbutyl group, a 1-ethyl-2-methylpropyl group, a 1,1-dimethylpentyl group, a 1,2-dimethylpentyl group, a 1,3-dimethylpentyl group, a 1,4-dimethylpentyl group, a 2,2-dimethylpentyl group, a 2,3-dimethylpentyl group, a 2,4-dimethylpentyl group, a 3,3-dimethylpentyl group, a 3,4-dimethylpentyl group, a 1-ethyl-1-methylbutyl group, a 1-ethyl-2-methylbutyl group, a 1-ethyl-3-methylbutyl group, a 2-ethyl-1-methylbutyl group, a 2-ethyl-3-methylbutyl group, a 1,1-dimethylhexyl group, a 1,2-dimethylhexyl group, a 1,3-dimethylhexyl group, a 1,4-dimethylhexyl group, a 1,5-dimethylhexyl group, a 2,2-dimethylhexyl group, a 2,3-dimethylhexyl group, a 2,4-dimethylhexyl group, a 2,5-dimethylhexyl group, a 3,3-dimethylhexyl group, a 3,4-dimethylhexyl group, a 3,5-dimethylhexyl group, a 4,4-dimethylhexyl group, a 4,5-dimethylhexyl group, a 1-ethyl-2-methylpentyl group, a 1-ethyl-3-methylpentyl group, a 1-ethyl-4-methylpentyl group, a 2-ethyl-1-methylpentyl group, a 2-ethyl-2-methylpentyl group, a 2-ethyl-3-methylpentyl group, a 2-ethyl-4-methylpentyl group, a 3-ethyl-1-methylpentyl group, a 3-ethyl-2-methylpentyl group, a 3-ethyl-3-methylpentyl group, a 3-ethyl-4-methylpentyl group, a 1-n-propyl-1-methylbutyl group, a 1-n-propyl-2-methylbutyl group, a 1-n-propyl-3-methylbutyl group, a 1-iso-propyl-1-methylbutyl group, a 1-iso-propyl-2-methylbutyl group, a 1-iso-propyl-3-methylbutyl group, a 1,1-diethylbutyl group, a 1,2-diethylbutyl group, a 1,1,2-trimethylpropyl group, a 1,2,2-trimethylpropyl group, a 1,1,2-trimethylbutyl group, a 1,1,3-trimethylbutyl group, a 1,2,3-trimethylbutyl group, a 1,2,2-trimethylbutyl group, a 1,3,3-trimethyl-butyl group, a 2,3,3-trimethylbutyl group, a 1,1,2-trimethylpentyl group, a 1,1,3-trimethylpentyl group, a 1,1,4-trimethylpentyl group, a 1,2,2-trimethylpentyl group, a 1,2,3-trimethylpentyl group, a 1,2,4-trimethylpentyl group, a 1,3,4-trimethylpentyl group, a 2,2,3-trimethylpentyl group, a 2,2,4-trimethylpentyl group, a 2,3,4-trimethylpentyl group, a 1,3,3-trimethylpentyl group, a 2,3,3-trimethylpentyl group, a 3,3,4-trimethylpentyl group, a 1,4,4-trimethylpentyl group, a 2,4,4-trimethylpentyl group, a 3,4,4-trimethylpentyl group, a 1-ethyl-1,2-dimethylbutyl group, a 1-ethyl-1,3-dimethylbutyl group, a 1-ethyl-2,3-dimethylbutyl group, a 2-ethyl-1,1-dimethylbutyl group, a 2-ethyl-1,2-dimethylbutyl group, a 2-ethyl-1,3-dimethylbutyl group, a 2-ethyl-2,3-dimethylbutyl group; and saturated cyclic alkyl groups having 5 to 10 carbon atoms in total, such as a cyclopentyl group, a cyclohexyl group, a methylcyclopentyl group, a methoxycyclopentyl group, a methoxycyclohexyl group, a methylcyclohexyl group, a 1,2-dimethylcyclohexyl group, a 1,3-dimethylcyclohexyl group, a 1,4-dimethylcyclohexyl group, an ethylcyclohexyl group.

Specific examples of the substituted or unsubstituted aryl group include aromatic hydrocarbons having not more than 20 carbon atoms in total, such as a phenyl group, a naphthyl group, an anthranyl group, a cyclopentadienyl group;

alkyl-substituted aryl groups having not more than 20 carbon atoms in total, such as a 2-methylphenyl group, a 3-methylphenyl group, a 4-methylphenyl group, a 2-ethylphenyl group, a propylphenyl group, a butylphenyl group, a hexylphenyl group, a cyclohexylphenyl group, an octylphenyl group, a 2-methyl-1-naphthyl group, a 3-methyl-1-naphthyl group, a 4-methyl-1-naphthyl group, a 5-methyl-1-naphthyl group, a 6-methyl-1-naphthyl group, a 7-methyl-1-naphthyl group, a 8-methyl-1-naphthyl group, a 1-methyl-2-naphthyl group, a 3-methyl-2-naphthyl group, a 4-methyl-2-naphthyl group, a 5-methyl-2-naphthyl group, a 6-methyl-2-naphthyl group, a 7-methyl-2-naphthyl group, a 8-methyl-2-naphthyl group, a 2-ethyl-1-naphthyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 3,6-dimethylphenyl group, a 2,3,4-trimethylphenyl group, a 2,3,5-trimethylphenyl group, a 2,3,6-trimethylphenyl group, a 2,4,5-trimethylphenyl group, a 2,4,6-trimethylphenyl group, a 3,4,5-trimethylphenyl group;

monoalkoxyaryl groups having not more than 20 carbon atoms in total wherein a substituted or unsubstituted alkyloxy group having not more than 10 carbon atoms is substituted, such as a 2-methoxyphenyl group, a 3-methoxyphenyl group, a 4-methoxyphenyl group, a 2-ethoxyphenyl group, a propoxyphenyl group, a butoxyphenyl group, a hexyloxyphenyl group, a cyclohexyloxyphenyl group, an octyloxyphenyl group, a 2-methoxy-1-naphthyl group, a 3-methoxy-1-naphthyl group, a 4-methoxy-1-naphthyl group, a 5-methoxy-1-naphthyl group, a 6-methoxy-1-naphthyl group, a 7-methoxy-1-naphthyl group, a 8-methoxy-1-naphthyl group, a 1-methoxy-2-naphthyl group, a 3-methoxy-2-naphthyl group, a 4-methoxy-2-naphthyl group, a 5-methoxy-2-naphthyl group, a 6-methoxy-2-naphthyl group, a 7-methoxy-2-naphthyl group, a 8-methoxy-2-naphthyl group, a 2-ethoxy-1-naphthyl group;

dialkoxyaryl groups having not more than 20 carbon atoms in total wherein a substituted or unsubstituted alkyloxy group having not more than 10 carbon atoms is substituted, such as a 2,3-dimethoxyphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 3,6-dimethoxyphenyl group, a 4,5-dimethoxy-1-naphthyl group, a 4,7-dimethoxy-1-naphthyl group, a 4,8-dimethoxy-1-naphthyl group, a 5,8-dimethoxy-1-naphthyl group, and a 5,8-dimethoxy-2-naphthyl group;

a trialkoxyaryl group having not more than 20 carbon atoms in total wherein a substituted or unsubstituted alkyloxy group having not more than 10 carbon atoms is substituted, such as a 2,3,4-trimethoxyphenyl group, a 2,3,5-trimethoxyphenyl group, a 2,3,6-trimethoxyphenyl group, a 2,4,5-trimethoxyphenyl group, a 2,4,6-trimethoxyphenyl group, a 3,4,5-trimethoxyphenyl group; and aryl groups having not more than 20 carbon atoms in total wherein a halogen atom is substituted, such as a chlorophenyl group, a dichlorophenyl group, a trichlorophenyl group, a bromophenyl group, a dibromophenyl group, an iodophenyl group, a fluorophenyl group, a chloronaphthyl group, a bromonaphthyl group, a difluorophenyl group, a trifluorophenyl group, a tetrafluorophenyl group, a pentafluorophenyl group.

Specific examples of the substituted or unsubstituted aralkyl group include a benzyl group, a phenethyl group, a phenylpropyl group, a naphthylethyl group, or a methyl group, an ethyl group, and a propyl group having an aryl group specifically mentioned as examples of the substituted or unsubstituted aryl group beforehand in a side chain.

Specific examples of the substituted or unsubstituted alkyloxy group include linear or branched alkoxy groups having 1 to 10 carbon atoms in total, such as a methoxy group, an ethoxy group, an n-propoxy group, an iso-propoxy group, an n-butoxy group, an iso-butoxy group, a tert-butoxy group, an n-pentyloxy group, an iso-pentyloxy group, an n-hexyloxy group, an iso-hexyloxy group, a 2-ethylhexyloxy group, a 3,5,5-trimethylhexyloxy group, an n-heptyloxy group, an n-octyloxy group, an n-nonyloxy group;

cycloalkoxy groups having 5 to 10 carbon atoms in total, such as a cyclopentyloxy group, a cyclohexyloxy group;

alkoxyalkoxy groups having 2 to 10 carbon atoms in total, such as a methoxymethoxy group, an ethoxymethoxy group, an ethoxyethoxy group, an n-propoxymethoxy group, an iso-propoxymethoxy group, an n-propoxyethoxy group, an iso-propoxyethoxy group, an n-butoxyethoxy group, an iso-butoxyethoxy group, a tert-butoxyethoxy group, an n-pentyloxyethoxy group, an iso-pentyloxyethoxy group, an n-hexyloxyethoxy group, an iso-hexyloxyethoxy group, an n-heptyloxyethoxy group; and aralkyloxy groups such as a benzyloxy group and the like.

Specific examples of the substituted or unsubstituted alkylthio group include linear or branched alkylthio groups having 1 to 10 carbon atoms in total, such as a methylthio group, an ethylthio group, an n-propylthio group, an iso-propylthio group, an n-butylthio group, an iso-butylthio group, a sec-butylthio group, a t-butylthio group, an n-pentylthio group, an iso-pentylthio group, an n-hexylthio group, an iso-hexylthio group, a 2-ethylhexylthio group, a 3,5,5-trimethylhexylthio group, an n-heptylthio group, an n-octylthio group, an n-nonylthio group;

cycloalkylthio groups having 5 to 10 carbon atoms in total, such as a cyclopentylthio group, a cyclohexylthio group;

alkoxyalkylthio groups having 2 to 10 carbon atoms in total, such as a methoxyethylthio group, an ethoxyethylthio group, an n-propoxyethylthio group, an iso-propoxyethylthio group, an n-butoxyethylthio group, an iso-butoxyethylthio group, a tert-butoxyethylthio group, an n-pentyloxyethylthio group, an iso-pentyloxyethylthio group, an n-hexyloxyethylthio group, an iso-hexyloxyethylthio group, an n-heptyloxyethylthio group;

aralkylthio groups such as a benzylthio group and the like; and alkylthioalkylthio groups having 2 to 10 carbon atoms in total, such as a methylthioethylthio group, an ethylthioethylthio group, an n-propylthioethylthio group, an iso-propylthioethylthio group, an n-butylthioethylthio group, an iso-butylthioethylthio group, a tert-butylthioethylthio group, an n-pentylthioethylthio group, an iso-pentylthioethylthio group, an n-hexylthioethylthio group, an iso-hexylthioethylthio group, an n-heptylthioethylthio group.

Specific examples of the substituted or unsubstituted aryloxy group include unsubstituted or alkyl-substituted aryloxy groups having not more than 20 carbon atoms in total, such as a phenyloxy group, a naphthyloxy group, an anthranyloxy group, a 2-methylphenyloxy group, a 3-methylphenyloxy group, a 4-methylphenyloxy group, a 2-ethylphenyloxy group, a propylphenyloxy group, a butylphenyloxy group, a hexylphenyloxy group, a cyclohexylphenyloxy group, an octylphenyloxy group, a 2-methyl-1-naphthyloxy group, a 3-methyl-1-naphthyloxy group, a 4-methyl-1-naphthyloxy group, a 5-methyl-1-naphthyloxy group, a 6-methyl-1-naphthyloxy group, a 7-methyl-1-naphthyloxy group, a 8-methyl-1-naphthyloxy group, a 1-methyl-2-naphthyloxy group, a 3-methyl-2-naphthyloxy group, a 4-methyl-2-naphthyloxy group, a 5-methyl-2-naphthyloxy group, a 6-methyl-2-naphthyloxy group, a 7-methyl-2-naphthyloxy group, a 8-methyl-2-naphthyloxy group, a 2-ethyl-1-naphthyloxy group, a 2,3-dimethylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, a 3,6-dimethylphenyloxy group, a 2,3,4-trimethylphenyloxy group, a 2,3,5-trimethylphenyloxy group, a 2,3,6-trimethylphenyloxy group, a 2,4,5-trimethylphenyloxy group, a 2,4,6-trimethylphenyloxy group, a 3,4,5-trimethylphenyloxy group;

monoalkoxyaryloxy groups having not more than 20 carbon atoms in total wherein a substituted or unsubstituted alkyloxy group having not more than 10 carbon atoms is substituted, such as a 2-methoxyphenyloxy group, a 3-methoxyphenyloxy group, a 4-methoxyphenyloxy group, a 2-ethoxyphenyloxy group, a propoxyphenyloxy group, a butoxyphenyloxy group, a hexyloxyphenyloxy group, a cyclohexyloxyphenyloxy group, an octyloxyphenyloxy group, a 2-methoxy-1-naphthyloxy group, a 3-methoxy-1-naphthyloxy group, a 4-methoxy-1-naphthyloxy group, a 5-methoxy-1-naphthyloxy group, a 6-methoxy-1-naphthyloxy group, a 7-methoxy-1-naphthyloxy group, a 8-methoxy-1-naphthyloxy group, a 1-methoxy-2-naphthyloxy group, a 3-methoxy-2-naphthyloxy group, a 4-methoxy-2-naphthyloxy group, a 5-methoxy-2-naphthyloxy group, a 6-methoxy-2-naphthyloxy group, a 7-methoxy-2-naphthyloxy group, a 8-methoxy-2-naphthyloxy group, a 2-ethoxy-1-naphthyloxy group;

dialkoxyaryloxy groups having not more than 20 carbon atoms in total wherein a substituted or unsubstituted alkyloxy group having not more than 10 carbon atoms is substituted, such as a 2,3-dimethoxyphenyloxy group, a 2,4-dimethoxyphenyloxy group, a 2,5-dimethoxyphenyloxy group, a 2,6-dimethoxyphenyloxy group, a 3,4-dimethoxyphenyloxy group, a 3,5-dimethoxyphenyloxy group, a 3,6-dimethoxyphenyloxy group, a 4,5-dimethoxy-1-naphthyloxy group, a 4,7-dimethoxy-1-naphthyloxy group, a 4,8-dimethoxy-1-naphthyloxy group, a 5,8-dimethoxy-1-naphthyloxy group, a 5,8-dimethoxy-2-naphthyloxy group;

trialkoxyaryloxy groups having not more than 20 carbon atoms in total wherein a substituted or unsubstituted alkyloxy group having not more than 10 carbon atoms is substituted, such as a 2,3,4-trimethoxyphenyloxy group, a 2,3,5-trimethoxyphenyloxy group, a 2,3,6-trimethoxyphenyloxy group, a 2,4,5-trimethoxyphenyloxy group, a 2,4,6-trimethoxyphenyloxy group, a 3,4,5-trimethoxyphenyloxy group; and aryloxy groups having not more than 20 carbon atoms in total wherein a halogen atom is substituted, such as a chlorophenyloxy group, a dichlorophenyloxy group, a trichlorophenyloxy group, a bromophenyloxy group, a dibromophenyloxy group, an iodophenyloxy group, a fluorophenyloxy group, a chloronaphthyloxy group, a bromonaphthyloxy group, a difluorophenyloxy group, a trifluorophenyloxy group, a tetrafluorophenyloxy group, a pentafluorophenyloxy group.

Specific examples of the substituted or unsubstituted arylthio group include unsubstituted or alkyl-substituted arylthio groups having not more than 20 carbon atoms in total, such as a phenylthio group, a naphthylthio group, an anthranylthio group, a 2-methylphenylthio group, a 3-methylphenylthio group, a 4-methylphenylthio group, a 2-ethylphenylthio group, a propylphenylthio group, a butylphenylthio group, a hexylphenylthio group, a cyclohexylphenylthio group, an octylphenylthio group, a 2-methyl-1-naphthylthio group, a 3-methyl-1-naphthylthio group, a 4-methyl-1-naphthylthio group, a 5-methyl-1-naphthylthio group, a 6-methyl-1-naphthylthio group, a 7-methyl-1-naphthylthio group, a 8-methyl-1-naphthylthio group, a 1-methyl-2-naphthylthio group, a 3-methyl-2-naphthylthio group, a 4-methyl-2-naphthylthio group, a 5-methyl-2-naphthylthio group, a 6-methyl-2-naphthylthio group, a 7-methyl-2-naphthylthio group, a 8-methyl-2-naphthylthio group, a 2-ethyl-1-naphthylthio group, a 2,3-dimethylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, a 3,6-dimethylphenylthio group, a 2,3,4-trimethylphenylthio group, a 2,3,5-trimethylphenylthio group, a 2,3,6-trimethylphenylthio group, a 2,4,5-trimethylphenylthio group, a 2,4,6-trimethylphenylthio group, a 3,4,5-trimethylphenylthio group;

monoalkoxyarylthio groups having not more than 20 carbon atoms in total wherein a substituted or unsubstituted alkyloxy group having not more than 10 carbon atoms is substituted, such as a 2-methoxyphenylthio group, a 3-methoxyphenylthio group, a 4-methoxyphenylthio group, a 2-ethoxyphenylthio group, a propoxyphenylthio group, a butoxyphenylthio group, a hexyloxyphenylthio group, a cyclohexyloxyphenylthio group, an octyloxyphenylthio group, a 2-methoxy-1-naphthylthio group, a 3-methoxy-1-naphthylthio group, a 4-methoxy-1-naphthylthio group, a 5-methoxy-1-naphthylthio group, a 6-methoxy-1-naphthylthio group, a 7-methoxy-1-naphthylthio group, a 8-methoxy-1-naphthylthio group, a 1-methoxy-2-naphthylthio group, a 3-methoxy-2-naphthylthio group, a 4-methoxy-2-naphthylthio group, a 5-methoxy-2-naphthylthio group, a 6-methoxy-2-naphthylthio group, a 7-methoxy-2-naphthylthio group, a 8-methoxy-2-naphthylthio group, a 2-ethoxy-1-naphthylthio group;

dialkoxyarylthio groups having not more than 20 carbon atoms in total wherein a substituted or unsubstituted alkyloxy group having not more than 10 carbon atoms is substituted, such as a 2,3-dimethoxyphenylthio group, a 2,4-dimethoxyphenylthio group, a 2,5-dimethoxyphenylthio group, a 2,6-dimethoxyphenylthio group, a 3,4-dimethoxyphenylthio group, a 3,5-dimethoxyphenylthio group, a 3,6-dimethoxyphenylthio group, a 4,5-dimethoxy-1-naphthylthio group, a 4,7-dimethoxy-1-naphthylthio group, a 4,8-dimethoxy-1-naphthylthio group, a 5,8-dimethoxy-1-naphthylthio group, a 5,8-dimethoxy-2-naphthylthio group;

trialkoxyarylthio groups having not more than 20 carbon atoms in total wherein a substituted or unsubstituted alkyloxy group having not more than 10 carbon atoms is substituted, such as a 2,3,4-trimethoxyphenylthio group, a 2,3,5-trimethoxyphenylthio group, a 2,3,6-trimethoxyphenylthio group, a 2,4,5-trimethoxyphenylthio group, a 2,4,6-trimethoxyphenylthio group, a 3,4,5-trimethoxyphenylthio group; and arylthio groups having not more than 20 carbon atoms in total wherein a halogen atom is substituted, such as a chlorophenylthio group, a dichlorophenylthio group, a trichlorophenylthio group, a bromophenylthio group, a dibromophenylthio group, an iodophenylthio group, a fluorophenylthio group, a chloronaphthylthio group, a bromonaphthylthio group, a difluorophenylthio group, a trifluorophenylthio group, a tetrafluorophenylthio group, a pentafluorophenylthio group. However, Y is not limited thereto.

Preferred examples of Y are as follows.

A preferred example thereof includes a hydrogen atom.

Furthermore, preferred examples of Y include a chlorine atom, a bromine atom, and an iodine atom as a halogen atom.

Preferred examples of the substituted or unsubstituted alkyl group include linear alkyl groups having 1 to 6 carbon atoms in total, such as a methyl group, an ethyl group, an n-propyl group, an n-butyl group, an n-pentyl group, an n-hexyl group;

branched alkyl groups having 3 to 6 carbon atoms in total, such as an isopropyl group, an isobutyl group, a sec-butyl group, an isopentyl group, a sec-pentyl group, a 1-methylpentyl group, a 2-methylpentyl group, a 3-methylpentyl group, a 4-methylpentyl group, a 1-ethylbutyl group, a 2-ethylbutyl group, a tert-butyl group, a tert-pentyl group, a 1,1-dimethylbutyl group, a 1,2-dimethylbutyl group, a 1,3-dimethylbutyl group, a 2,3-dimethylbutyl group; and saturated cyclic alkyl groups having 5 to 6 carbon atoms in total, such as a cyclopentyl group, a cyclohexyl group.

Preferred examples of the substituted or unsubstituted aryl group include aromatic hydrocarbons having not more than 12 carbon atoms in total, such as a phenyl group, a naphthyl group, a cyclopentadienyl group;

alkyl-substituted aryl groups having not more than 12 carbon atoms in total, such as a 2-methylphenyl group, a 3-methylphenyl group, a 4-methylphenyl group, a 2-ethylphenyl group, a propylphenyl group, a butylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 3,6-dimethylphenyl group, a 2,3,4-trimethylphenyl group, a 2,3,5-trimethylphenyl group, a 2,3,6-trimethylphenyl group, a 2,4,5-trimethylphenyl group, a 2,4,6-trimethylphenyl group, a 3,4,5-trimethylphenyl group;

monoalkoxyaryl groups having not more than 12 carbon atoms in total wherein a substituted or unsubstituted alkyloxy group having not more than 6 carbon atoms is substituted, such as a 2-methoxyphenyl group, a 3-methoxyphenyl group, a 4-methoxyphenyl group, a 2-ethoxyphenyl group, a propoxyphenyl group, a butoxyphenyl group;

dialkoxyaryl groups having not more than 12 carbon atoms in total wherein a substituted or unsubstituted alkyloxy group having not more than 6 carbon atoms is substituted, such as a 2,3-dimethoxyphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 3,6-dimethoxyphenyl group; and aryl groups having not more than 12 carbon atoms in total wherein a halogen atom is substituted, such as a chlorophenyl group, a dichlorophenyl group, a trichlorophenyl group, a bromophenyl group, a dibromophenyl group, an iodophenyl group, a fluorophenyl group, a chloronaphthyl group, a bromonaphthyl group, a difluorophenyl group, a trifluorophenyl group, a tetrafluorophenyl group, a pentafluorophenyl group.

Preferred examples of the substituted or unsubstituted aralkyl group include an aralkyl group having not more than 12 carbon atoms in total, such as a benzyl group, a phenethyl group, a phenylpropyl group.

Preferred examples of the substituted or unsubstituted alkyloxy group include linear or branched alkoxy groups having 1 to 6 carbon atoms in total, such as a methoxy group, an ethoxy group, an n-propoxy group, an iso-propoxy group, an n-butoxy group, an iso-butoxy group, a tert-butoxy group, an n-pentyloxy group, an iso-pentyloxy group, an n-hexyloxy group, an iso-hexyloxy group;

cycloalkoxy groups having 5 to 6 carbon atoms in total, such as a cyclopentyloxy group, a cyclohexyloxy group; and alkoxyalkoxy groups having 2 to 6 carbon atoms in total, such as a methoxymethoxy group, an ethoxymethoxy group, an ethoxyethoxy group, an n-propoxymethoxy group, an iso-propoxymethoxy group, an n-propoxyethoxy group, an iso-propoxyethoxy group, an n-butoxyethoxy group, an iso-butoxyethoxy group, a tert-butoxyethoxy group.

Preferred examples of the substituted or unsubstituted alkylthio group include linear or branched alkylthio groups having 1 to 6 carbon atoms in total, such as a methylthio group, an ethylthio group, an n-propylthio group, an iso-propylthio group, an n-butylthio group, an iso-butylthio group, a sec-butylthio group, a t-butylthio group, an n-pentylthio group, an iso-pentylthio group, an n-hexylthio group, an iso-hexylthio group;

cycloalkylthio groups having 5 to 6 carbon atoms in total, such as a cyclopentylthio group, a cyclohexylthio group;

alkoxyalkylthio groups having 2 to 6 carbon atoms in total, such as a methoxyethylthio group, an ethoxyethylthio group, an n-propoxyethylthio group, an iso-propoxyethylthio group, an n-butoxyethylthio group, an iso-butoxyethylthio group, a tert-butoxyethylthio group; and alkylthioalkylthio group halving 2 to 6 carbon atoms in total, such as a methylthioethylthio group, an ethylthioethylthio group, an n-propylthioethylthio group, an iso-propylthioethylthio group, an n-butylthioethylthio group, an iso-butylthioethylthio group, a tert-butylthioethylthio group.

Preferred examples of the substituted or unsubstituted aryloxy group include unsubstituted or alkyl-substituted aryloxy groups having not more than 12 carbon atoms in total, such as a phenyloxy group, a naphthyloxy group, a 2-methylphenyloxy group, a 3-methylphenyloxy group, a 4-methylphenyloxy group, a 2-ethylphenyloxy group, a propylphenyloxy group, a butylphenyloxy group, a hexylphenyloxy group, a cyclohexylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, a 3,6-dimethylphenyloxy group, a 2,3,4-trimethylphenyloxy group, a 2,3,5-trimethylphenyloxy group, a 2,3,6-trimethylphenyloxy group, a 2,4,5-trimethylphenyloxy group, a 2,4,6-trimethylphenyloxy group, a 3,4,5-trimethylphenyloxy group;

monoalkoxyaryloxy groups having not more than 12 carbon atoms in total wherein a substituted or unsubstituted alkyloxy group having not more than 6 carbon atoms is substituted, such as a 2-methoxyphenyloxy group, a 3-methoxyphenyloxy group, a 4-methoxyphenyloxy group, a 2-ethoxyphenyloxy group, a propoxyphenyloxy group, a butoxyphenyloxy group, a hexyloxyphenyloxy group, a cyclohexyloxyphenyloxy group;

dialkoxyaryloxy groups having not more than 12 carbon atoms in total wherein a substituted or unsubstituted alkyloxy group having not more than 6 carbon atoms is substituted, such as a 2,3-dimethoxyphenyloxy group, a 2,4-dimethoxyphenyloxy group, a 2,5-dimethoxyphenyloxy group, a 2,6-dimethoxyphenyloxy group, a 3,4-dimethoxyphenyloxy group, a 3,5-dimethoxyphenyloxy group, a 3,6-dimethoxyphenyloxy group; and aryloxy groups having not more than 12 carbon atoms in total wherein a halogen atom is substituted, such as a chlorophenyloxy group, a dichlorophenyloxy group, a trichlorophenyloxy group, a bromophenyloxy group, a dibromophenyloxy group, an iodophenyloxy group, a fluorophenyloxy group, a chloronaphthyloxy group, a bromonaphthyloxy group, a difluorophenyloxy group, a trifluorophenyloxy group, a tetrafluorophenyloxy group, a pentafluorophenyloxy group.

Preferred examples of the substituted or unsubstituted arylthio group include unsubstituted or alkyl-substituted arylthio groups having not more than 12 carbon atoms in total, such as a phenylthio group, a naphthylthio group, a 2-methylphenylthio group, a 3-methylphenylthio group, a 4-methylphenylthio group, a 2-ethylphenylthio group, a propylphenylthio group, a butylphenylthio group, a hexylphenylthio group, a cyclohexylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, a 3,6-dimethylphenylthio group, a 2,3,4-trimethylphenylthio group, a 2,3,5-trimethylphenylthio group, a 2,3,6-trimethylphenylthio group, a 2,4,5-trimethylphenylthio group, a 2,4,6-trimethylphenylthio group, a 3,4,5-trimethylphenylthio group;

monoalkoxyarylthio groups having not more than 12 carbon atoms in total wherein a substituted or unsubstituted alkyloxy group having not more than 6 carbon atoms is substituted, such as a 2-methoxyphenylthio group, a 3-methoxyphenylthio group, a 4-methoxyphenylthio group, a 2-ethoxyphenylthio group, a propoxyphenylthio group, a butoxyphenylthio group, a hexyloxyphenylthio group, a cyclohexyloxyphenylthio group;

dialkoxyarylthio groups having not more than 12 carbon atoms in total wherein a substituted or unsubstituted alkyloxy group having not more than 6 carbon atoms is substituted, such as a 2,3-dimethoxyphenylthio group, a 2,4-dimethoxyphenylthio group, a 2,5-dimethoxyphenylthio group, a 2,6-dimethoxyphenylthio group, a 3,4-dimethoxyphenylthio group, a 3,5-dimethoxyphenylthio group, a 3,6-dimethoxyphenylthio group, a 4,5-dimethoxy-1-naphthylthio group, a 4,7-dimethoxy-1-naphthylthio group, a 4,8-dimethoxy-1-naphthylthio group, a 5,8-dimethoxy-1-naphthylthio group, a 5,8-dimethoxy-2-naphthylthio group; and arylthio groups having not more than 12 carbon atoms in total wherein a halogen atom is substituted, such as a chlorophenylthio group, a dichlorophenylthio group, a trichlorophenylthio group, a bromophenylthio group, a dibromophenylthio group, an iodophenylthio group, a fluorophenylthio group, a chloronaphthylthio group, a bromonaphthylthio group, a difluorophenylthio group, a trifluorophenylthio group, a tetrafluorophenylthio group, a pentafluorophenylthio group.

More preferred examples of Y are as follows.

A more preferred example includes a hydrogen atom.

Further, examples of the halogen atom include a chlorine atom and a bromine atom.

More preferred examples of the substituted or unsubstituted alkyl group include a linear or branched alkyl group having 1 to 3 carbon atoms in total, such as a methyl group, an ethyl group, and an iso-propyl group.

More preferred examples of the substituted or unsubstituted aryl group include aromatic hydrocarbons having not more than 12 carbon atoms in total, such as a phenyl group, a naphthyl group, a cyclopentadienyl group;

alkyl-substituted aryl groups having not more than 9 carbon atoms in total, such as a 2-methylphenyl group, a 3-methylphenyl group, a 4-methylphenyl group, a 2-ethylphenyl group, a propylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 3,6-dimethylphenyl group;

monoalkoxyaryl groups having not more than 9 carbon atoms in total wherein a substituted or unsubstituted alkyloxy group having not more than 3 carbon atoms is substituted, such as a 2-methoxyphenyl group, a 3-methoxyphenyl group, a 4-methoxyphenyl group, a 2-ethoxyphenyl group, a propoxyphenyl group; and aryl groups having not more than 12 carbon atoms in total wherein a halogen atom is substituted, such as a chlorophenyl group, a dichlorophenyl group, a trichlorophenyl group, a bromophenyl group, a dibromophenyl group, a chloronaphthyl group, a bromonaphthyl group.

More preferred examples of the substituted or unsubstituted aralkyl group include an aralkyl group having not more than 9 carbon atoms in total, such as a benzyl group, a phenethyl group, and a phenylpropyl group.

More preferred examples of the substituted or unsubstituted alkyloxy group include linear or branched alkoxy groups having 1 to 3 carbon atoms in total, such as a methoxy group, an ethoxy group, an iso-propoxy group; and cycloalkoxy groups having 5 to 6 carbon atoms in total, such as a cyclopentyloxy group, a cyclohexyloxy group.

More preferred examples of the substituted or unsubstituted alkylthio group include linear or branched alkylthio groups having 1 to 3 carbon atoms in total, such as a methylthio group, an ethylthio group, an n-propylthio group, and an iso-propylthio group;

cycloalkylthio groups having 5 to 6 carbon atoms in total, such as a cyclopentylthio group, and a cyclohexylthio group; and alkylthioalkylthio groups having 2 to 6 carbon atoms in total, such as a methylthioethylthio group, an ethylthioethylthio group, an n-propylthioethylthio group, an iso-propylthioethylthio group, an n-butylthioethylthio group, an iso-butylthioethylthio group, and a tert-butylthioethylthio group.

More preferred examples of the substituted or unsubstituted aryloxy group include unsubstituted or alkyl-substituted aryloxy groups having not more than 9 carbon atoms in total, such as a phenyloxy group, a naphthyloxy group, a 2-methylphenyloxy group, a 3-methylphenyloxy group, a 4-methylphenyloxy group, a 2-ethylphenyloxy group, a propylphenyloxy group, a 2,4-dimethylphenyloxy group, a 2,5-dimethylphenyloxy group, a 2,6-dimethylphenyloxy group, a 3,4-dimethylphenyloxy group, a 3,5-dimethylphenyloxy group, a 3,6-dimethylphenyloxy group;

monoalkoxyaryloxy groups having not more than 9 carbon atoms in total wherein a substituted or unsubstituted alkyloxy group having not more than 3 carbon atoms is substituted, such as a 2-methoxyphenyloxy group, a 3-methoxyphenyloxy group, a 4-methoxyphenyloxy group, a 2-ethoxyphenyloxy group, a propoxyphenyloxy group; and aryloxy groups having not more than 12 carbon atoms in total wherein a halogen atom is substituted, such as a chlorophenyloxy group, a dichlorophenyloxy group, a trichlorophenyloxy group, a bromophenyloxy group, a dibromophenyloxy group, a chloronaphthyloxy group, a bromonaphthyloxy group.

More preferred examples of the substituted or unsubstituted arylthio group include unsubstituted or alkyl-substituted arylthio groups having not more than 9 carbon atoms in total, such as a phenylthio group, a 2-methylphenylthio group, a 3-methylphenylthio group, a 4-methylphenylthio group, a 2-ethylphenylthio group, a propylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, a 3,6-dimethylphenylthio group;

monoalkoxyarylthio groups having not more than 9 carbon atoms in total wherein a substituted or unsubstituted alkyloxy group having not more than 3 carbon atoms is substituted, such as a 2-methoxyphenylthio group, a 3-methoxyphenylthio group, a 4-methoxyphenylthio group, a 2-ethoxyphenylthio group, a propoxyphenylthio group; and arylthio groups having not more than 12 carbon atoms in total wherein a halogen atom is substituted, such as a chlorophenylthio group, a dichlorophenylthio group, a trichlorophenylthio group, a bromophenylthio group, a dibromophenylthio group, a chloronaphthylthio group, a bromonaphthylthio group.

Furthermore, if n-p is an integer of 2 or more, Y may be bonded to each other to form a ring structure with the intermediary of a metal atom M. That is, a plurality of Y may be bonded to each other to form a ring containing a metal atom M.

In the polymerizable composition of the present invention containing the above-described components, from the viewpoint of better balance among the refractive index, the mechanical properties, and the color, the molar ratio of the thiol groups in the polymerizable composition may be 1 or more, based on the total of the iso(thio)cyanate groups, the epoxy groups, the episulfide groups, the carbon-carbon double bonds, and the thietanyl groups in the thietane compound containing no metal atom. That is, the molar ratio expressed by SH groups/(NCO groups and/or NCS groups+ epoxy groups+episulfide groups+carbon-carbon double bonds+thietanyl groups) may be 1 or more.

Next, the non-metal thietane compound will be described.

The non-metal thietane compound contains one or more thietanyl groups in the molecule. Further, as the non-metal thietane compound, a compound having any structure which is compatible with the additive of the present invention can be used, but it is preferably a compound having two or more thietanyl groups in total.

Specific examples of the non-metal thietane compound include sulfide-based thietane compounds such as bisthietanyl sulfide, bis(3-thietanylthio)methane, 3-(((3'-thietanylthio)methylthio)methylthio)thietane;

polysulfide-based thietane compounds such as bis(3-thietanyl)disulfide, bis(3-thietanyl)trisulfide, bis(3-thietanyl)tetrasulfide, bis(3-thietanyl)pentasulfide; etc.

Among these exemplified compounds, at least one is preferably selected from the group consisting of bis(3-thietanyl)disulfide, bis(3-thietanyl)tetrasulfide, bis(3-thietanylthio)methane, 3'-(((3-thietanylthio)methylthio)methylthio) thietane, tetrakis(3-thietanylthio)tin, tris(3-thietanylthio) bismuth, and bis(3-thietanylthio)dithiastannolane.

Further, preferred compounds among these exemplified compounds are bis(3-thietanyl)sulfide, bis(3-thietanylthio) methane, bis(3-thietanyl)disulfide, bis(3-thietanyl)tetrasulfide, bis(3-thietanylthio)dithiastannolane, and tetrakis(3-thietanylthio)tin, and more preferred compounds are bis(3-thietanyl)disulfide, bis(3-thietanylthio)dithiastannolane, and tetrakis(3-thietanylthio)tin.

The polymerizable composition of the present invention may contain a polymerization catalyst as described later, if desired.

The kind and the amount of the polymerization catalysts which are in the present invention, if necessary, and the kind and the ratio of the monomers vary depending on the structure of the compound constituting the polymerizable composition, and thus cannot be clearly defined. However, as the kinds of the polymerization catalyst, amines, phosphines, organic acids and salts, esters, anhydrides thereof, inorganic acids, quaternary ammonium salts, quaternary phosphonium salts, tertiary sulfonium salts, secondary iodonium salts, Lewis acids, radical polymerization catalysts, cationic polymerization catalysts, or the like are usually used.

The polymerization catalyst may be used alone or in a mixture of two or more kinds thereof. A mixture of at least two kinds of the polymerization catalysts having different reactivities may be preferable for improving the monomer handleability, and the optical physical properties, color, transparency, and optical strain (striation) of the obtained resin in some cases.

Among the compounds exemplified above as the polymerization catalyst, preferred examples include organotin compounds such as dimethyltin dichloride, dibutyltin dichloride, dibutyltin dilaurate, dibutyltin diacetate, tetrachlorotin, dibutyltin oxide and diacetoxytetrabutylstannoxane; trifluoroacetic acid, trichloroacetic acid, trifluoroacetic anhydride, ethyl trifluoroacetate, sodium trifluoroacetate, trihalogenoacetic acids, and esters, anhydrides and salts thereof;

p-toluenesulfonic acid, methanesulfonic acid, trihalogenomethanesulfonic acids such as trifluoromethanesulfonic acid, trifluoromethanesulfonic anhydride, ethyl trifluoromethanesulfonate, sodium trifluoromethanesulfonate and esters, anhydrides and salts thereof;

Lewis acids such as boron trihalides and complexes thereof, such as a boron trifluoride, various boron trifluoride complexes such as a boron trifluoride diethyl ether complex, a boron trifluoride piperidine complex, a boron trifluoride ethylamine complex, a boron trifluoride acetic acid complex, a boron trifluoride phosphoric acid complex, a boron trifluoride t-butyl methyl ether complex, a boron trifluoride dibutyl ether complex, a boron trifluoride THF complex, a boron trifluoride methyl sulfide complex, a boron trifluoride phenol complex, and various boron trichloride complexes, and preferably dimethyltin dichloride, trifluoromethane sulfonic, and esters, anhydrides and salts thereof, and various boron trifluoride complexes; and radical polymerization catalysts such as 2,2'-azobis(2-cyclopropylpropionitrile), 2,2'-azobis(4-methoxy-2,4-dimethylvaleronitrile), 2,2'-azobis(2,4-dimethylvaleronitrile), t-butylperoxy-2-ethyl hexanoate, n-butyl-4,4'-bis(t-butylperoxy) valerate, t-butyl peroxybenzoate.

The amount of the polymerization catalyst of the polymerizable composition according to the present invention to be added is used in the range from 0.0001 to 10% by weight, preferably 0.001 to 10% by weight, more preferably from 0.01% by weight to 5% by weight, and most preferably from 0.01% by weight to 1% by weight, based on the total amount of the polymerizable composition.

With the amount of the polymerization catalyst to be added in this range, a sufficiently cured resin can be prepared, and pot life can be maintained more reliably. Also, the obtained resin may have better transparency and optical physical properties in some cases.

The polymerization catalyst may be added directly to the polymerizable compositions or some of the compounds thereof, or may be dissolved or dispersed in another compound, and then added. In some cases, the polymerization catalyst is preferably dissolved or dispersed in another compound, and then added, for obtaining good results in some cases. Furthermore, the polymerization catalyst is preferably added under a nitrogen atmosphere or a dry gas atmosphere for obtaining good results in some cases. In order to improve the performance of the resulting resin, the amount of the unreactive groups remaining in the resin is preferably 0.5% by weight or less, and more preferably 0.4% by weight or less, based on the total weight of the resin.

The polymerizable composition of the present invention may include other polymerizable compounds, in addition to the compound represented by the general formula (1), within the range not interfering with the desired effects of the present invention.

Examples of the polymerizable compound include various polymerizable monomers or polymerizable oligomers which are known in the art. Examples thereof include a (meth) acrylic acid ester compound, a vinyl compound, an oxetane compound, and the like.

The content of the polymerizable compound (at least one selected from an isocyanate compound, an episulfide compound, an epoxy compound, and a thietane compound) comprised in the total weight of the polymerizable compounds containing a thiol compound, which is contained in the polymerizable composition of the present invention, is usually not more than 90% by weight, preferably not more than 70% by weight, and more preferably not more than 60% by weight, from the viewpoint of obtaining a high refractive index material, taking into consideration that an increased amount of the polymerizable compound to be added usually results in reduction in the refractive index of the polymerizable composition. On the other hand, from the viewpoint of adjusting to a desired refractive index by making a balance with physical properties (heat resistance, mechanical strength, and the like) other than a refractive index, the additive of the present invention can be mixed with the polymerizable compound at any mixing ratio for adjusting it to a desired physical property allowing it to be dissolved in the polymerizable composition. In addition, if the polymerizable compound is contained in the polymerizable composition of the present invention, the content of the polymerizable compounds is not particularly limited in their lower limits.

For the purpose of following improvement of the resin obtained by curing the polymerizable composition or following improvement of handling ability thereof, it may be preferable to subject the polymerizable composition of the invention to the means and operations which are generally used upon synthesizing organic compounds, such as purification or washing, thermal insulation, cold storage, filtration or depressurization treatment, or to add known compounds or the like as stabilizers or resin modifying agents. The improvement of the resin or the improvement of handling ability thereof includes further adjustment of the optical properties of the resin such as a refractive index and the Abbe number; the adjustment of various properties of the resin such as color, light resistance or weather resistance, heat resistance, impact resistance, hardness, specific gravity, linear expansion coefficients, polymerization shrinkage ratios, water absorbability, hygroscopicity, chemical resistance, viscoelasticity; the adjustment of transmittance or transparency; and the adjustment of the viscosity and handling ability of other storage or transportation method of the polymerizable composition. Examples of compounds added for improving stability such as long-term preservation stability, polymerization stability, thermal stability include a polymerization retardant, a polymerization inhibitor, a deoxidant, an antioxidant, and the like.

Purification of the polymerizable composition is a means for improving the transparency of the resin obtained by curing or for increasing the purity of the resin to improve the color thereof. As a method for purifying the polymerizable composition containing the compound having the structure represented by the general formula (1) of the present invention, any known method, for example, recrystallization, column chromatography (a silica gel method, an activated carbon method, an ion-exchange resin method, or the like), extraction, or the like, may be performed with any timing as long as the transparency and the color of the resin obtained by curing the composition generated by purification are improved.

The method for washing the polymerizable composition is a means for improving the transparency or the color of the resin obtained by curing, but examples thereof include a method in which, at the time when the synthesized polymerizable composition is taken out or subsequently, the composition is washed with a polar and/or nonpolar solvent to remove or reduce a resin transparency inhibitor, for example, an inorganic salt used for synthesizing the polymerizable composition or secondarily produced in synthesizing the composition, such as an ammonium salt and the like. Although the solvent used depends, but is not limited, upon the polymerizable composition to be cleaned, the polarity of a solution containing the polymerizable composition, and the like, a solvent which can dissolve a component to be removed, and which is incompatible with the polymerizable composition to be cleaned and the solution containing the polymerizable composition is preferably used. The solvent may be used singly or in a mixture of two or more kinds thereof. Although the amount of a component to be removed depends upon the purpose and application, it is preferably as low as possible. The results may be obtained at an amount of usually 5000 ppm or less, and more preferably 1000 ppm or less in some cases.

The hot insulation/cold insulation/filtration method for the polymerizable composition is a means for improving the transparency or the color of the resin obtained by curing, but is generally carried out with timing when or after the synthesized polymerizable composition is taken out. In the hot insulation method, for example, when the polymerizable composition is crystallized to deteriorate handleability during storage, the polymerizable composition is melted by heating within a range causing no deterioration in the performance of the polymerizable composition and the resin obtained by curing the polymerizable composition. Although the heating temperature range and heat melting method depend upon the compound constituting the polymerizable composition to be handled and thus cannot be clearly defined, the heating temperature is generally in a range of the solidification point+50° C., and preferably the solidification point+20° C. In this method, the composition may be melted by mechanically stirring with a stirring device or bubbling with an inert gas for moving an internal liquid. The cold insulation method is generally performed for improving the preservation stability of the polymerizable composition. However, when the composition has a high melting point, consideration must be given to the storage temperature in order to improve the handleability after crystallization. Although the cold insulation temperature depends upon the structure and preservation stability of the compound constituting the polymerizable composition to be handled and thus cannot be clearly defined, the polymerizable composition is generally required to be preserved at a temperature no higher than a temperature for maintaining the stability of the polymerizable composition containing the compound represented by the general formula (1).

Furthermore, in the case where the polymerizable composition according to the present invention is a polymerizable composition for the use in optical applications, it is required to have high transparency, and thus it is typically preferable that the polymerizable composition is filtered with a filter having a small pore size. Although the pore size of the filter used is usually from 0.05 to 10 μm, and the pore size is preferably from 0.05 to 5 μm, and more preferably 0.1 to 5 μm, from the viewpoint of processibility and performance. In many cases, filtration of the polymerizable composition of the present invention produces good results without exception. As for the filtration temperature, although a low filtration temperature near a solidification temperature produces more desirable results in some cases, filtration is preferably performed at a temperature causing no trouble in the filtration work when solidification proceeds during filtration.

The treatment under reduced pressure is a means for removing a solvent, dissolved gas, or odor which deteriorates the performance of the resin generally produced by curing the polymerizable composition. Since a dissolved solvent generally decreases the refractive index of the resulting resin and deteriorates the heat resistance thereof, the dissolved solvent must be removed as much as possible. Although the allowable amount of the dissolved solvent depends upon the structure of the compound constituting the polymerizable composition to be handled and the structure of the dissolved solvent is not limited, the allowable amount is usually 1% or less, and preferably 5000 ppm or less. The dissolved gas inhibits polymerization or causes the problem of mixing bubbles in the resulting resin, and thus is preferably removed. Particularly, a moisture gas such as water vapor or the like is preferably removed by bubbling with a dry gas. The amount of the dissolved gas can be set depending upon the structure of the compound constituting the polymerizable composition, and the physical properties, the structure, and the type of the dissolved gas.

Typical examples of the method for preparing the polymerizable composition of the present invention include a method using the additive of the present invention, a thiol compound, and other appropriate components, and if necessary, using the above-described various polymerizable compounds in combination, and then if necessary, adding the polymerization catalyst, and then mixing and dissolving it, or the like.

When curing and molding the polymerizable composition of the present invention, according to purposes, various materials such as a stabilizer, a resin modifier, a chain extender, a crosslinking agent, a photostabilizer including a HALS-based photostabilizer or the like, an ultraviolet ray absorber typically including a benzotriazole-based ultraviolet ray absorber and the like, an antioxidant typically including a hindered phenol-based antioxidant and the like, a coloring inhibitor, a dye or bluing agent typically including an anthraquinone disperse dye and the like, a filler, an external mold releasing agent typically including a silicone-based external mold releasing agent, or an internal mold releasing agent typically including a surfactant such as acidic phosphate, a quaternary ammonium salt, a quaternary phosphonium salt, an adhesion improving agent may be added, as in the known molding methods. Here, the internal mold releasing agent also includes those exhibiting a releasing effect among various additives as described above.

Although the addition amount of the various additives which can be added depends upon the type, the structure, and the effect of each additive and thus cannot be clearly defined, the addition amount usually in the range of 0.001% by weight to 10% by weight, and preferably 0.01 to 5% by weight, based on the total weight of the polymerizable composition, is used. The dye is preferably used in the range from 1 ppb to 100 ppm. Within these ranges, a sufficiently cured resin can be prepared, and the obtained resin may have better transparency and optical physical properties in some cases.

Next, the resin according to the present invention will be described.

The resin and the transparent member comprising the resin according to the present invention are obtained by polymerization of the polymerizable composition.

Furthermore, the method for preparing the resin (and the transparent member) according to the present invention involves a step for polymerizing the polymerizable composition according to the present invention. Examples of such a method include various methods known in the art, which are employed in the preparation of plastic lenses, but a typically example thereof is casting polymerization.

That is, the polymerizable composition of the present invention prepared by the above-described method is degassed under a reduced pressure or filtered off, as required, and then the polymerizable composition is poured into a mold, and heated to carry out polymerization, if desired. In this case, it is preferable to carry out polymerization by slowly heating from a low temperature to a high temperature.

The mold for molding as described above is composed of, for example, two pieces of mirror surface-ground molds via a gasket made of polyethylene, an ethylene vinyl acetate copolymer, polyvinyl chloride, and the like. Typical examples of the mold include, but not limited to, a combined mold of glass and glass, as well as a combined mold of glass and a plastic plate, a combined mold of glass and a metal plate, and the like. The mold may include two pieces of molds fixed by a tape such as a polyester adhesive tape and the like. In addition, a known method such as mold release treatment and the like may be performed for the mold, if desired.

When carrying out casting polymerization, the polymerization temperature is affected by the polymerization conditions such as the kind of the polymerization initiator. Thus, it is not particularly limited, but it is usually from −50° C. to 200° C., preferably from −20° C. to 170° C., and more preferably from 0 to 150° C.

The polymerization temperature affects the polymerization time, but it is usually from 0.01 to 200 hours and preferably from 0.05 to 100 hours. Polymerization can also be carried out by temperature maintenance or by combination of several temperatures such as temperature elevation, temperature dropping, or the like, if desired.

Furthermore, the polymerizable composition of the present invention can be polymerized by applying the active energy ray such as an electron beam, an ultraviolet ray, and a visible light. At this time, a radical polymerization catalyst or a cationic polymerization catalyst for initiating polymerization by the active energy ray is used, if desired.

Here, Tg is a temperature that is measured by a TMA (Thermal Mechanical Analysis) penetration method, obtained from the cross-points in a TMA curve, which corresponds a heat distortion beginning temperature.

After curing, the obtained resin and the optical lens comprising the resin are cured, they may be subjected to an annealing treatment, if desired. Furthermore, for purposes of giving anti-reflection, offering high hardness, improving abrasion resistance, offering anti-fogging property or offering fashionability, various known physical or chemical treatments such as a surface polishing, antistatic treatment, a hard coat treatment, a non-reflection coat treatment, an anti-reflection treatment, a tinting treatment, a photochromic treatment (for example, a photochromic lens treatment and the like) may be performed, if desired.

Furthermore, for the obtained resin and the optical lens comprising the resin, coating layer(s) may be formed on either or both of the surfaces and used, if desired. Hereinbelow, the optical lens will be described by way of an example. Examples of the coating layer include a primer layer, a hard coat layer, an anti-reflection layer, an anti-fogging coat film layer, an anti-fouling layer, a water-repellent layer, and the like. These coating layers may be used alone, respectively, or a plurality of coating layers may be formed into a multi-layer and used. In the case of providing the coating layers on both sides, the coating layers provided on each side may either be the same as or different from each other.

For those coating layers, there may be employed in combination known additive agents for the purpose of improving the performance of lenses. As the additive, specifically, an UV absorber for the purpose of protecting the lenses or the eyes from UV light;

an infrared ray absorber for the purpose of protecting the eyes from infrared rays, a photostabilizer or antioxidant for the purpose of improving the weatherability of the lenses;

a dye, a pigment, or the like for the purpose of increasing fashionability of the lenses, or the like may be used, and photochromic dyes, photochromic pigments, an antistatic agent, and other various additives may also be used. Further, various leveling agents for the purpose of improving the coatability may also be used for the layer to be coated by application.

The primer layer is usually formed between the hard coat layer to be described later and the optical lenses. The primer layer is a coating layer provided for the purpose of improving the adhesiveness between the hard coat layer and lenses, and it is also possible to improve the impact resistance.

For the primer layer, any material can be used as long as it provides high adhesiveness to the obtained optical lens, and usually employed are an urethane-based resin, an epoxy-based resin, a polyester-based resin, a melanin-based resin, a primer composition containing polyvinyl acetal as a main component, and the like. For the purpose of adjusting the viscosity of the composition, an appropriate solvent can be used, which does not affect the lens, in the primer composition. Of course, the solvent may not be used.

The primer composition can be formed by either of an application process or a dry process. If the application process is used, a spin coat, a dip coat, or the like is applied on the lens by means of a known application process, and then solidified to form a primer layer. If the dry process is used, the primer layer is formed by means of dry processes such as a CVD process, a vacuum deposition process. In order to improve the adhesiveness when the primer layer is formed, if necessary, the surfaces of the lens may be subjected to preliminary treatments such as alkali treatment, plasma treatment, and ultraviolet ray treatment.

The hard coat layer is a coating layer provided for the purpose of giving functions such as an anti-scratching property, abrasion resistance, humidity resistance, hot-water resistance, heat resistance, weather resistance to the lens surface.

For the hard coat layer, an organosilicon compound having curing property, and a hard coat composition having oxide fine particles of one element selected from the group consisting of Si, Al, Sn, Sb, Ta, Ce, La, Fe, Zn, W, Zr, In, and Ti and/or fine particles constituted of a composite oxide of two or more elements selected from the group consisting of those elements, are generally used. The fine particles composed of the oxide fine particles and/or the composite oxide may be used singly, or in combination of two or more kinds thereof in the hard coat composition. The hard coat composition preferably includes, in addition to said components, at least one selected from amines, amino acids, metal acetyl acetate complexes, metal salts of organic acid, pechloric acids, pechloric acid salts, acids, metal chlorides, and polyfunctional epoxy compounds. For the hard coat composition, an appropriate solvent which does not affect the lens may be used. Of course, the solvent may not be used.

The hard coat layer is usually formed by applying a hard coat composition using a known coating process such as spin coat, dip coat, and then curing it. Examples of the curing process include a thermal curing process, a curing process using an energy ray such as an ultraviolet ray and a visible light. In order to inhibit the generation of the interference fringe, the refractive index of the hard coat layer is preferably in the range of the refractive index of the lens ±(plus/minus) 0.1.

The anti-reflection layer is usually formed on said hard coat layer, if desired. There are an inorganic type and an organic type for the anti-reflection layer, and the inorganic type is provided by the use of inorganic oxide such as $SiO_2$, $TiO_2$ in accordance with the dry method such as a vacuum evaporation technique, a sputtering method, an ion plating method, an ion beam assist method, a CVD method. The organic type is formed using a composition which includes an organosilicon compound and a silica-based fine particle having internal cavity in accordance with the wet method.

The anti-reflection layer may be a mono-layer or a multi-layer, and if it is used as a mono-layer, it is preferable that its refractive index is lower than that of the hard coat layer by at least 0.1 or more. In order to exhibit the anti-reflection function more effectively, a multi-layer is preferable as the anti-reflection layer. In this case, a layer having a low refractive index and a layer having a high refractive index are stacked alternately. Also, in this case, the difference in the refractive indices of the layer having a low refractive index and the layer having a high refractive index is preferably 0.1 or more. Examples of the high refractive index film include films of ZnO, $TiO_2$, $CeO_2$, $Sb_2O_5$, $SnO_2$, $ZrO_2$, $Ta_2O_5$, and the like, and examples of the low refractive index film include a $SiO_2$ film, and the like.

If necessary, an anti-fogging coat layer, an anti-staining layer, and a water-repellent layer may be further formed on the anti-reflection layer. As the means for forming the anti-fogging coat layer, the anti-staining layer, and the water-repellent layer, methods and materials for the treatment thereof, or the like are not particularly limited as long as it is within the scope of not adversely affecting the anti-reflection properties, and a known anti-fogging coat treatment method, an anti-staining treatment method, a water-repellent treatment method, and materials may be employed.

For example, examples of the methods for anti-fogging coat and anti-fouling treatment include a method of covering a surface with a surfactant, a method of adding a hydrophilic layer on a surface to give absorptivity, a method of covering a surface with a fine unevenness to increase absorptivity, a method of using the activity of a photo-catalyst to give absorptivity, a method of performing an ultra-water-repellency treatment to prevent attachment of water drops, and the like.

Furthermore, examples of the water-repellency treatment method include a method of forming a water-repellent treatment layer by deposition or sputtering with a fluorine-containing silane compound, or the like, and a method of dissolving a fluorine-containing silane compound in a solvent, and then performing coating to form a water-repellency treated layer, and the like.

In addition, the obtained resin and the optical lens comprising the resin may be tinted using a colorant for the purpose so as to provide fashionability or photochromic property, or the like, and used. Hereinbelow, the tinting of optical lens will be described by way of an example.

Tinting of the optical lens can be carried out in accordance with a known tinting method, and is carried out generally by any one of the following methods:

(a) a method of immersing a lens in a dye liquid;

(b) a method of subjecting coating with the use of a coating agent containing a colorant, or providing a coating layer which can be tinted, and tinting the provided coating layer;

(c) a method of polymerizing monomer raw materials in which materials which can be tinted are contained; and (d) a method of heating a sublimation colorant to allow sublimation.

The method (a) is generally a method including immersing a lens material finished on a predetermined optical surface in a tinting solution in which the colorant to be used is dissolved or uniformly dispersed (tinting process), and then fixing the colorant on the lens by heating (annealing process after tinting), if desired.

The colorant used in the tinting process is, for example, a known colorant, and is not particularly limited. However, an oil-soluble dye or a disperse dye is usually used. The solvent used in the tinting process is not particularly limited as long as it is the solvent in which the colorant to be used can be dissolved or uniformly dispersed therein.

In the tinting process, a surfactant for dispersing the dye in a tinting solution or a carrier which encourages tinting may also be added, if desired.

In the tinting process, a colorant and a surfactant that is added, if necessary, are dispersed in water, or a mixture of water and an organic solvent, to prepare a tinting bath. An optical lens is immersed in the tinting bath to perform tinting at a predetermined temperature for a predetermined time. The tinting temperature and time vary depending on the color density, but they are usually 120° C. or lower and several minutes to several tens of hours, respectively. Tinting is performed at a concentration of the tinting bath of around 0.01 to 10% by weight. Furthermore, if it is difficult to tint, the tinting is performed under pressure. The annealing process, that is performed, if necessary, after tinting, is a process in which the tinted lens greige is subject to heat treatment. The heat treatment is, for example, to allow a predetermined retention in a furnace such as an infrared heating furnace, a resistant heating furnace, and the like at an atmosphere, after removing water remaining on the surface of the tinted lens greige in the tinting process with a solvent, or the like, or removing the solvent by blowing air. The annealing process after tinting prevents the tinted lens greige from decoloration (decoloration-preventing treatment), as well as removes the moisture penetrated into the inside of the lens greige upon tinting.

The method (b) is not a method for directly tinting a plastic lens material, but a method including coating a plastic lens with an organic coating liquid in which a colorant is dispersed or dissolved, and then subjecting to a curing treatment to form a tinted coating layer on a lens surface, or a method including forming a coating layer which can be tinted on a plastic lens surface, and then performing the method (a), that is, a method including immersing the plastic lens in a tinting solution, and subjecting to heating to be tinted.

The method (c) is a method including preliminarily dissolving a dye in monomer raw materials for a plastic lens, and then carrying out polymerization. The colorant to be used is not particularly limited as long as it can be uniformly dissolved or dispersed in monomer raw materials to the extent of not deteriorating the optical properties.

Examples of the method (d) include the following (d1) to (d3):

(d1) a method which includes sublimating a solid sublimation colorant and tinting a plastic lens;

(d2) a method which includes facing a plastic lens to a substrate to which a solution containing a sublimation dye is applied in a non-contacting manner, and heating the substrate and the lens to allow tinting; and (d3) a method which includes transferring a colored layer containing a sublimation colorant and a transfer layer including an adhesive layer to a plastic lens, and then heating to be tinted.

The resin of the invention and the optical lenses comprising the resin may be tinted in accordance with any of those methods. The colorant to be used is not particularly limited as long as it is a colorant having a sublimating property.

Also, by adding the additive of the present invention, improvement of the refractive indices of the resin and the transparent member can be encouraged, and the resin cured product and the optical member obtained from the polymerizable composition containing the additive can have a refractive index as high as a refractive index of 1.6 to 1.8.

Examples of the optical components according to the present invention include various plastic lens such as a spectacle lens for vision correction, a lens for photographic instruments, a fresnel lens for liquid crystal projectors, a lenticular lens, a contact lens;

a sealing material for light emitting diodes (LED);

an optical waveguide;

an optical adhesive used for the junction of an optical lens or an optical waveguide;

an anti-reflection film used for optical lenses;

a transparent coating or transparent substrate used for liquid crystal display device members such as a substrate, a light guiding plate, a film, a sheet; etc.

EXAMPLES

Hereinafter, the present invention will be explained in more detail with reference to Preparative Examples and Examples, but is not limited to these Examples.

Reference Preparative Example 1

Synthesis of 3-mercaptothietane (a method described in Patent Document 4 (Japanese Patent Laid-open Publication No. 2003-327583))

190 g (2.50 moles) of thiourea, 253 g of a 35% hydrochloric acid, and 250 g of water were introduced into a reactor equipped with a stirrer and a thermometer, and stirred to give a reaction liquid. While stirring the reaction liquid, 156 g (1.73 moles) of 3-thietanol was added dropwise to the reaction liquid over 1 hour. After the dropwise addition was completed, the solution was stirred and reacted at 30° C. for 24 hours, and then 177 g of 24% ammonia water was added dropwise thereto over 1 hour. The solution was further reacted at 30° C. for 15 hours, and then allowed to stand for taking out an organic layer (lower layer) to obtain 134 g of a crude product. The resulting crude product was distilled off under a reduced pressure to collect a fraction with a boiling point of 40° C./106 Pa, thereby obtaining 3-mercaptothietane as a desired product of a colorless transparent liquid.

Reference Preparative Example 2

Synthesis of tetrakis(3-thietanylthio)tin 11.15 g (0.105 mole) of 3-mercaptothietane prepared in Reference Preparative Example 1 was introduced into 50 g of pure water. Subsequently, 41.2 g (0.103 mole) of a 10% NaOH aqueous solution was introduced dropwise thereto at room temperature over 40 minutes. Then, the reaction liquid was rised temperature to 30° C. and 65.2 g (corresponding to 0.025 mole of tin tetrachloride) of an aqueous solution of 10% tin tetrachloride was added dropwise thereto at the same temperature over 4 hours. After the dropwise addition was completed, the solution was further stirred at the same temperature for 2 hours. 100 ml of chloroform was added to the reaction mixture, and the organic layer and the water layer were separated. The organic layer was washed with 100 ml of pure water twice, and then dried over anhydrous sodium sulfate. The solvent was distilled off from the extract to obtain tetrakis(3-thietanylthio)tin (13.4 g) represented by following chemical formula.

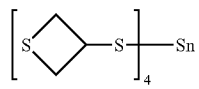

Reference Preparative Example 3

Synthesis of tris(3-thietanylthio)antimony (III)

71.3 g (0.66 mole) of 3-mercaptothietane prepared in Reference Preparative Example 1 was added to 106.9 g of pure water, and the mixture was cooled to 15° C. Subsequently, 87.7 g (0.66 mole) of an aqueous solution of 30 weight % sodium hydroxide was added dropwise thereto over 1 hour. Thereafter, 250.0 g (corresponding to 0.22 mole of antimony trichloride) of an ethanol solution of 20.0 weight % antimony trichloride was added dropwise thereto to at the same temperature over 2 hours. After completion of the dropwise addition, the solution was further stirred at the same temperature for 2 hours.

The solid material was collected by filtration from the reaction, and repeatedly washed with water to remove a salt secondarily produced. After further washing with methanol, the product was dried under reduced pressure.

The reaction mixture after drying was dissolved in 500 g of chloroform, and the insoluble material was removed by filtration. The solution was concentrated, and hexane was then added thereinto. The precipitate was collected by filtration and then dried under reduced pressure to obtain tris(3-thietanylthio)antimony (III) (87.6 g; yield 91%) represented by the following formula as a desired product.

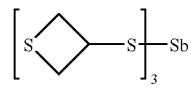

Preparative Example 1

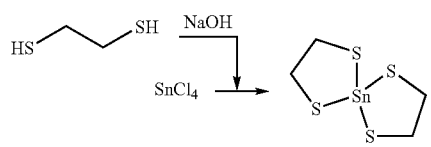

1,2-Ethanedithiol (54 g, a commercial available product) and degassed water (182 g) were added dropwise to a reactor, and then a 31% aqueous sodium hydroxide solution (148 g) and degassed water (100 g) were added dropwise thereto under cooling (8° C.). Also, a 24% aqueous tin (IV) chloride solution (313 g) was added dropwise thereto over 2 hours at the same temperature. The resulting precipitate was collected by filtration, washed with water, and washed with methanol to obtain a crude product (213 g). To the crude product was added a 10-fold weight of chloroform, the mixture was heated and dissolved, and the insoluble material was removed by filtration. The obtained filtrate was concentrated, and then hexane was introduced thereinto. The precipitate was collected by filtration and then dried under reduced pressure to obtain 83 g (yield 95%) of a desired product.

Melting point: 182.2-183.3° C.

$^1$H-NMR (solvent: CDCl$_3$, Internal standard material: TMS): δ 3.22 (8H).

IR (Universal ATR method): 624, 653, 837, 919, 1238, 1278, 1406 cm$^{-1}$.

FD-MS: m/z 304(M$^+$).

Preparative Example 2

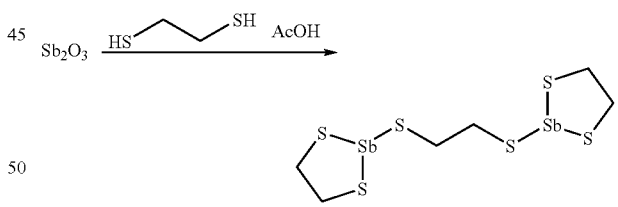

1,2-Ethanedithiol (10 g, a commercial available product) and antimony trioxide (5 g) were introduced into a reactor, and acetic acid (0.5 g) was further introduced thereinto. The mixture was rised temperature to 40° C. and reacted for additional 4 hours and at 70° C. for 2 hours. After the reaction mixture was cooled, chloroform was added thereto for crystallization, and the precipitate was collected by filtration and dried under reduced pressure to obtain 8.6 g (yield 96%) of a desired product.

Melting point: 130.7-132.9° C.

$^1$H-NMR (solvent: DMSO-d$_6$, Internal standard material: TMS): δ 3.2 to 3.6 (12H).

IR (Universal ATR method): 438, 641, 661, 834, 918, 1287, 1406, 2888 cm$^{-1}$.

FD-MS: m/z 519(M$^+$)

Preparative Example 3

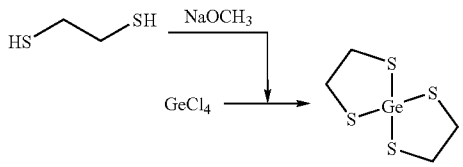

1,2-Ethanedithiol (20.5 g; a commercial available product) and ethanol (100 ml) were introduced into a reactor, and then a 28% sodium methoxide-methanol solution (79.5 g) was added dropwise thereto under cooling (5 to 10° C.). Further, a germanium (IV) tetrachloride (21 g)-ethanol solution was added dropwise thereto. The resulting precipitate was collected by filtration, washed, and then dissolved in chloroform, and the insoluble material was removed by filtration. The resulting solution was concentrated, and then hexane was introduced thereinto. The precipitate was collected by filtration and dried under reduced pressure to obtain 20 g (yield 77%) of a desired product.

Melting point: 165° C.

$^1$H-NMR (solvent: CDCl$_3$, Internal standard material: TMS): δ 3.22 (8H).

IR (Universal ATR method): 426, 639, 662, 845, 927, 1247, 1283, 1411, 2913, 2949 cm$^{-1}$.

EI-MS: m/z 258(M$^+$).

Elemental Analysis Calculated Value Ge 28%, Found Value Ge: 29%.

Preparative Example 4

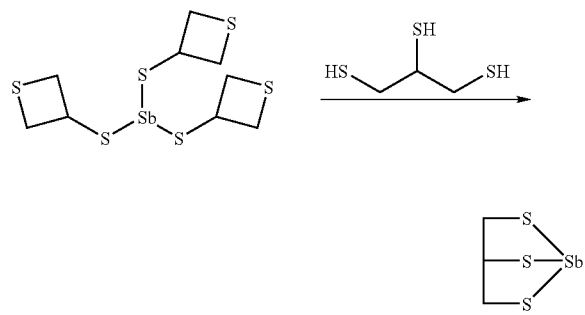

1,2,3-Propanetrithiol (16.2 g) and Chloroform (200 g) were introduced into a reactor, and then a solution of tris(3-thietanylthio)antimony (III) (50 g) in chloroform (200 g) were added dropwise thereto at 20° C. The precipitate was collected by filtration and dried under reduced pressure to obtain 28.8 g (yield 93%) of a desired product.

Melting point: 214° C.

$^1$H-NMR (solvent: DMSO-d$_6$, Internal standard material: TMS): δ 2.82 (2H), 3.39 (2H), 5.90 (1H).

IR (Universal ATR method): 576, 596, 779, 954, 1260, 1409, 2809, 2895 cm$^{-1}$.

Elemental Analysis: Calculated Value Sb 47%, Found Value Sb: 45%.

Preparative Example 5

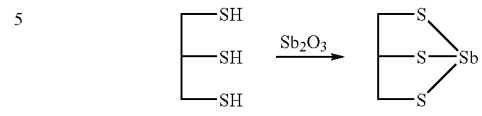

1,2,3-Propanetrithiol (10.2 g), antimony trioxide (5 g), and acetic acid (1 g) were introduced into a reactor. The mixture was slowly rised temperature to 70° C. and reacted at 70° C. for 2 hours. Further, antimony trioxide (5 g) was added thereto, and reacted at 70° C. for 2 hours. The reaction mixture was cooled and then suspended by addition of methanol. Then, the filtrate was collected and dried under reduced pressure to obtain 16.4 g (yield 92%) of a desired product.

$^1$H-NMR (solvent: DMSO-d$_6$, Internal standard material: TMS): δ 2.82 (2H), 3.39 (2H), 5.90 (1H).

IR (Universal ATR method): 576, 596, 779, 953, 1259, 1409, 2809, 2894 cm$^{-1}$.

Elemental Analysis: Calculated Value: Sb 47%, Found Value Sb: 49%.

The physical properties of the molded bodies (optical lenses) obtained in the following Examples were evaluated according to the following methods.

Transparency: Transparency was confirmed with the naked eyes using a slide projector.

Refractive index: Measurement was conducted using a Pulfrich refractometer at 20° C.

Heat resistance: A TMA penetration method

Example 1-A1

The compound (0.5 g) obtained in Preparative Example 1 was dissolved in 4-mercaptomethyl-1,8-dimercapto-3,6-dithiaoctane (2.0 g) at 20° C., and then a mixture (2.3 g) of 2,5-bis(isocyanatomethyl)-bicyclo[2.2.1] heptane and 2,6-bis(isocyanatomethyl)-bicyclo[2.2.1] heptane was further mixed therewith to give a uniform solution. This mixed solution was degassed for 10 minutes under reduced pressure, and then charged into a mold composed of a glass mold and a tape. This mold was introduced to a polymerization oven, and slowly rised temperature from 25° C. to 120° C. over 24 hours to carry out polymerization. After the polymerization was completed, a mold was taken from the oven and released to obtain a molded body.

The values of the physical properties of the obtained molded body are shown in Table 1.

Examples 1-A2 to 1-A6

In the same manner as in Example 1-A1 except for using the composition of Table 1, a mixed solution and a molded body were prepared. The values of the physical properties of the obtained molded body are shown in Table 1.

Example 1-B1

The compound (0.25 g) obtained in Preparative Example 2 was added and dissolved in a mixture (2.3 g) of 4-mercaptomethyl-1,8-dimercapto-3,6-dithiaoctane (2.0 g), 2,5-bis (isocyanatomethyl)-bicyclo[2.2.1]heptane, and 2,6-bis(isocyanatomethyl)-bicyclo[2.2.1]heptane at 20° C. to give a uniform solution (polymerizable composition). This solution was degassed for 10 minutes under reduced pressure and then charged into a mold composed of a glass mold and a tape. This mold was introduced to a polymerization oven, and slowly rised temperature from 25° C. to 120° C. over 24 hours to carry out polymerization. After the polymerization was completed, a mold was taken from the oven and released to obtain a molded body.

The values of the physical properties of the obtained molded body are shown in Table 1.

Examples 1-B2 to 1-B3

In the same manner as in Example 1-B1 except for using the composition of Table 1, a mixed solution and a molded body were prepared. The values of the physical properties of the obtained molded body are shown in Table 1.

Comparative Example 1

In the same manner as in Example 1-A1 except that the compound obtained in Preparative Example 1 or 2 was not used and dibutyltin dichloride was added at 230 ppm relative to the isocyanate compound as a polymerization catalyst, a mixed solution and a molded body were prepared. The values of the physical properties of the obtained molded body are shown in Table 1.

Example 2-A1

The compound (0.5 g) obtained in Preparative Example 1 was added and dissolved in a mixture (0.4 g) of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane, and a mixture (5.0 g) of bis(2,3-epithiopropyl)disulfane. To this was added a mixture (0.1 g) of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane, in which N,N-dicyclohexylamine (1000 ppm relative to the epithio compound) had been dissolved, thereby giving a uniform solution. This solution was degassed for 10 minutes at 400 Pa and then charged into a mold composed of a glass mold and a tape. This mold was introduced to a polymerization oven, and slowly rised temperature from 30° C. to 80° C. over 24 hours to carry out polymerization. After the polymerization was completed, a mold was taken from the oven and released to obtain a molded body.

The values of the physical properties of the obtained molded body are shown in Table 2.

Examples 2-A2 to 2-A3

In the same manner as in Example 2-A1 except for using the composition of Table 2, a mixed solution and a molded

TABLE 1

| | Composition (% by weight) | | | | Polymerization catalyst ppm | Optical physical property | | | Heat resistance Tg (°) | Specific gravity |
|---|---|---|---|---|---|---|---|---|---|---|
| | Compound of Preparative Example 1 | Compound of Preparative Example 2 | Thiol compound A | Isocyanate compound I | | Refractive Index (ne) | Abbe Number | Transparency | | |
| Comparative Example 1 | 0% | 0% | 46% | 54% | DBC 230 | 1.623 | 38.1 | Transparent | 113.3 | 1.31 |
| Example 1-A1 | 10% | 0% | 41% | 49% | None | 1.639 | 35.7 | Transparent | 117.4 | 1.36 |
| Example 1-A2 | 15% | 0% | 39% | 46% | None | 1.647 | 34.7 | Transparent | 114.0 | 1.38 |
| Example 1-A3 | 20% | 0% | 37% | 43% | None | 1.655 | 34.8 | Transparent | Not measured | Not measured |
| Example 1-A4 | 26% | 0% | 34% | 40% | None | 1.664 | 32.5 | Transparent | Not measured | Not measured |
| Example 1-A5 | 28.5% | 0% | 32.7% | 38.8% | None | 1.670 | 32.4 | Transparent | Not measured | Not measured |
| Example 1-A6 | 31.5% | 0% | 31.5% | 37.0% | None | 1.675 | 30.0 | Transparent | Not measured | Not measured |
| Example 1-B1 | 0% | 3% | 44% | 53% | None | 1.629 | 37.1 | Transparent | 115.7 | 1.32 |
| Example 1-B2 | 0% | 5.4% | 43.2% | 51.4% | None | 1.633 | 36.1 | Transparent | 115.2 | 1.34 |
| Example 1-B3 | 0% | 10% | 41% | 49% | None | 1.645 | 35.0 | Transparent | 107.1 | 1.37 |

A: 4-Mercaptomethyl-1,8-dimercapto-3,6-dithiaoctane
I: Bis(isocayanatomethyl)bicyclo[2.2.1]heptane
DBC: Dibutyltin dichloride
Polymerization condition: 25° C./8 hr→(25→120° C./24 hr)→120° C./4 hr

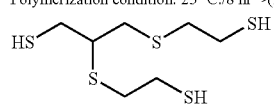

(A)

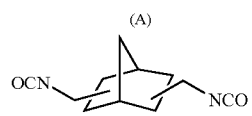

(I)

body were prepared. The values of the physical properties of the obtained molded body are shown in Table 2.

Examples 2-B1 to 2-B6

In the same manner as in Example 2-A1 except that the compound of Preparative Example 1 was changed to the compound of Preparative Example 2 and the composition of Table 2 was used, a mixed solution and a molded body were prepared. The values of the physical properties of the obtained molded body are shown in Table 2.

Comparative Example 2

In the same manner as in Example 2-A1 except that the compound obtained in Preparative Example 1 or 2 was not used and the composition of Table 2 was used, a mixed solution and a molded body were prepared. The values of the physical properties of the obtained molded body are shown in Table 2.

Example 3-A1

N,N-dicyclohexylamine (13 mg), 3-mercaptothietane (0.7 g), bis(3-thietanyl)disulfide (1.04 g), and the compound (1.0 g) obtained in Preparative Example 1 were mixed and dissolved at 70° C. to give a uniform solution. This solution was degassed for 10 minutes at 400 Pa, and then charged into a mold composed of a glass mold and a tape. This mold was introduced to a polymerization oven, and slowly rised temperature from 80° C. to 120° C. over 32 hours to carry out polymerization. After the polymerization was completed, a mold was taken from the oven and released to obtain a molded body.

The values of the physical properties of the obtained molded body are shown in Table 3.

Examples 3-A2 to 3-A7

In the same manner as in Example 3-A1 except for using the composition of Table 3, a mixed solution and a molded body were prepared. The values of the physical properties of the obtained molded body are shown in Table 3.

TABLE 2

|  | Composition (% by weight) | | | | Polymerization | | Optical physical property | | Transpa- rency | Heat resist- ance (°C.) | Speci- fic gravity |
|---|---|---|---|---|---|---|---|---|---|---|---|
|  | Compound of Preparative Example 1 | Compound of Preparative Example 2 | Thiol compound B | Epitho compound X | catalyst | ppm | Refractive Index (ne) | Abbe Number | | | |
| Comparative Example 2 | 0% | 0% | 9% | 91% | DCH | 1000 | 1.737 | 32.3 | Transparent | 72.5 | 1.47 |
| Example 2-A1 | 8.4% | 0% | 8.3% | 83.3% | DCH | 1000 | 1.747 | 30.3 | Transparent | 91.6 | 1.50 |
| Example 2-A2 | 15% | 0% | 8% | 77% | DCH | 1000 | 1.753 | 29.3 | Transparent | 87.7 | 1.53 |
| Example 2-A3 | 21.5% | 0% | 7.2% | 71.4% | DCH | 1000 | 1.757 | 28.0 | Transparent | 84.9 | 1.56 |
| Example 2-B1 | 0% | 8% | 8% | 84% | DCH | 1000 | 1.752 | 30.3 | Transparent | 89.9 | 1.52 |
| Example 2-B2 | 0% | 12% | 8% | 80% | DCH | 500 | 1.759 | 29.0 | Transparent | 92.2 | 1.53 |
| Example 2-B3 | 0% | 18.5% | 7.4% | 74.1% | DCH | 250 | 1.768 | 27.2 | Transparent | 82.4 | 1.56 |
| Example 2-B4 | 0% | 19% | 8% | 73% | DCH | 400 | 1.771 | 27.6 | Transparent | 88.3 | 1.58 |
| Example 2-B5 | 0% | 31% | 7% | 62% | DCH | 400 | 1.792 | 25.5 | Transparent | 62.3 | 1.65 |
| Example 2-B6 | 0% | 34% | 6% | 60% | DCH | 550 | 1.800 | 24.6 | Transparent | 71.2 | 1.69 |

B: Mixture of 5,7-dimercaptomethyl-1,11-dimercapto-3,6,9-trithiaundecane, 4,7-dimercaptomethyl-1,11-dimercapto-3,6,9-trithiaundecane, and 4,8-mercaptomethyl-1,11-dimercapto-3,6,9-triethiaundecane
X: Bis(2,3-epithiopropyl)disulfane
DCH: N,N-Dicyclohexylamine
Polymerication condition: 30° C./48 h→(30→80° C./24 hr)→80° C./24 hr, annealing: 120° C./2 hr

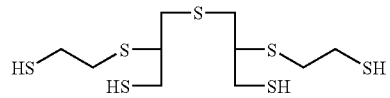

(B)

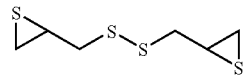

(X)

Comparative Examples 3-1 to 3-4

In the same manner as in Example 3-A1 except that the compound of Preparative Example 1 was not used and the composition of Table 3 was used, a mixed solution and a molded body were prepared. The values of the physical properties of the obtained molded body are shown in Table 3.

TABLE 3

| | Composition (% by weight) | | | | Optical physical property | | | | |
|---|---|---|---|---|---|---|---|---|---|
| | Compound of Preparative Example 1 | Thiol compound C | Thietane compound Y | Added materials ppm | Refractive Index (ne) | Abbe Number | Transparency | Heat resistance Tg (° C.) | Specific gravity |
| Comparative Example 3-1 | 0% | 0% | 100% | $CF_3SO_3H$ 5000 | 1.737 | 33 | Transparent | Not Measured | 1.47 |
| Comparative Example 3-2 | 0% | 40% | 60% | DCH 5000 | | | Not thickened | | |
| Comparative Example 3-3 | 0% | 11% | 89% | DCH 5000 | | | Not thickened | | |
| Comparative Example 3-4 | 0% | 25% | 75% | DCH 5000 | | | Not thickened | | |
| Example 3-A1 | 37% | 25% | 38% | DCH 5000 | 1.764 | 27.6 | Transparent | 48.8 | 1.62 |
| Example 3-A2 | 22% | 15% | 63% | DCH 5000 | 1.753 | 28.7 | Transparent | 74.6 | 1.57 |
| Example 3-A3 | 24% | 9% | 67% | DCH 5000 | 1.762 | 28.8 | Transparent | 90.2 | 1.59 |
| Example 3-A4 | 15% | 22% | 63% | DCH 5000 | 1.748 | 30.9 | Transparent | 60.9 | 1.53 |
| Example 3-A5 | 26% | 19% | 55% | DCH 5000 | 1.756 | 28.2 | Transparent | 63.1 | 1.58 |
| Example 3-A6 | 26% | 19% | 55% | DCH 5000 | 1.760 | 29.3 | Transparent | 69.3 | 1.58 |
| Example 3-A7 | 42% | 15% | 43% | DCH 5000 | 1.775 | 27.1 | Transparent | 66.7 | 1.67 |

C: 3-Mercaptothietane
Y: Bis(3-thietanyl)disulfide
DCH: N,N-Dicyclohexylmethylamine
Polymerization condition: 80° C./12 hr→(80° C.→120° C.)/32 hr→ 120° C./24 hr

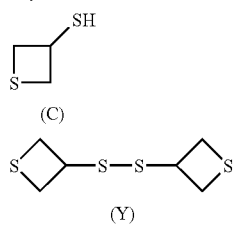

Example 4-A1

The compound (0.1 g) of Preparative Example 1 was dissolved in 4-mercaptomethyl-1,8-dimercapto-3,6-dithiaoctane (1.0 g) at 20° C., and then Celloxide 2021P [manufactured by DAICEL CHEMICAL INDUSTRIES, LTD.: (3',4'-epoxycyclohexane)methyl-3,4-epoxycyclohexanecarboxylate] (1.5 g) was mixed therewith to give a uniform solution. This mixed solution was degassed for 10 minutes at 400 Pa, and then charged into a mold composed of a glass mold and a tape. This mold was introduced to a polymerization oven, and slowly rised temperature from 40° C. to 120° C. over 20 hours to carry out polymerization. After the polymerization was completed, a mold was taken from the oven and released to obtain a molded body.

The values of the physical properties of the obtained molded body are shown in Table 4.

Examples 4-A2 to 4-A4

In the same manner as in Example 4-A1 except for using the composition of Table 4, a mixed solution and a molded body were prepared. The values of the physical properties of the obtained molded body are shown in Table 4.

Examples 4-B1 to 4-B2

In the same manner as in Example 4-A1 except that the compound of Preparative Example 1 was changed to the compound of Preparative Example 2 and the composition of Table 4 was used, a mixed solution and a molded body were prepared. The values of the physical properties of the obtained molded body are shown in Table 4.

Comparative Example 4

In the same manner as in Example 4-A1 except that the compound obtained in Preparative Example 1 or 2 was not used and the composition of Table 4 was used, a mixed solution and a molded body were prepared. The values of the physical properties of the obtained molded body are shown in Table 4.

TABLE 4

| | Composition (% by weight) | | | | | Optical physical property | | | | |
|---|---|---|---|---|---|---|---|---|---|---|
| | Compound of Preparative Example 1 | Compound of Preparative Example 2 | Thiol compound A | Epoxy compound Z | Polymerization catalyst ppm | Refractive Index (ne) | Abbe Number | Transparency | Heat resistance Tg (° C.) | Specific gravity |
| Comparative Example 4 | 0% | 0% | 41% | 59% | (1) 1000 | 1.605 | 44.4 | Transparent | 66.0 | 1.30 |
| Example 4-A1 | 4% | 0% | 40% | 56% | (2) 5000 | 1.613 | 41.7 | Transparent | 66.3 | 1.32 |
| Example 4-A2 | 9% | 0% | 37% | 54% | (2) 5000 | 1.620 | 40.1 | Transparent | 69.4 | 1.35 |
| Example 4-A3 | 17% | 0% | 34% | 49% | (2) 5000 | 1.632 | 37.2 | Transparent | Not measured | Not measured |
| Example 4-A4 | 23% | 0% | 32% | 45% | (2) 5000 | 1.643 | 35.6 | Transparent | 82.7 | 1.42 |
| Example 4-B1 | 0% | 5% | 39% | 56% | (1) 1000 | 1.614 | 41.1 | Transparent | 63.5 | 1.33 |
| Example 4-B2 | 0% | 9% | 37% | 54% | (1) 1000 | 1.622 | 39.3 | Transparent | 61.9 | 1.35 |

A: 4-Mercaptomethyl-1,8-dimercapto-3,6-dithiaoctane
Z: Celloxide 2021P (DAICEL CHEMICAL INDUSTRIES, LTD.): [(3',4'-epoxycyclohexane)methyl-3,4-epoxycyclohexanecarboxylate]
Polymerization catalyst (1): 2-mercapto-1-methylimizadloe, Polymerization catalyst (2): Bu4PBr
Polymerization condition: 40° C./8 hr→(40→120° C./20 hr)→120° C./5 hr

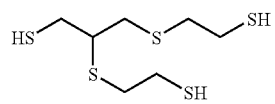

(A)

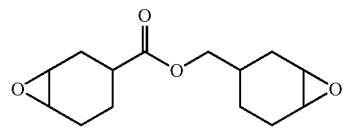

(Z)

Example 5-A1

3-Mercaptothietane (1.0 g), tetrakis(3-thietanylthio)tin (3.0 g), and the compound (1.7 g) of Preparative Example 1 were mixed, and then heated and dissolved at 70° C. to give a uniform solution. This solution was degassed for 10 minutes at 400 Pa, and then charged into a mold composed of a glass mold and a tape. This mold was introduced to a polymerization oven, and slowly rised temperature from 80° C. to 120° C. over 12 hours to carry out polymerization. After the polymerization was completed, a mold was taken from the oven and released to obtain a molded body.

The values of the physical properties of the obtained molded body are shown in Table 5.

Example 5-B1

In the same manner as in Example 5-A1 except that the compound of Preparative Example 1 was changed to the compound of Preparative Example 2 and the composition of Table 5 was used, a mixed solution and a molded body were prepared. The values of the physical properties of the obtained molded body are shown in Table 5.

Comparative Examples 5-1 to 5-2

In the same manner as in Example 5-A1 except that the compound obtained in Preparative Example 1 or 2 was not used and the composition of Table 5 was used, a mixed solution and a molded body were prepared. The values of the physical properties of the obtained molded body are shown in Table 5.

TABLE 5

| | Composition (% by weight) | | | | Optical physical property | | | | |
|---|---|---|---|---|---|---|---|---|---|
| | Compound of Preparative Example 1 | Compound of Preparative Example 2 | Thiol compound C | Metal thietane W | Added materials ppm | Refractive Index (ne) | Abbe Number | Transparency | Heat resistance Tg (° C.) | Specific gravity |
| Comparative Example 5-1 | 0% | 0% | 18% | 82% | None | 1.776 | 26.3 | Transparent | Not measured | Not measured |
| Comparative Example 5-2 | 0% | 0% | 29% | 71% | None | 1.765 | 27.1 | Transparent | 64.5 | Not measured |
| Example 5-A1 | 30% | 0% | 18% | 52% | None | 1.792 | 24.3 | Transparent | Not measured | Not measured |
| Example 5-B1 | 0% | 28% | 15% | 57% | None | 1.810 | Not measured | Transparent | Not measured | Not measured |

C: 3-Mercaptothietane
W: Tetrakis (3-thietanylthio)tin
Polymerization condition: 80° C./24 hr→(80° C.→120° C.)/12 hr→120° C./15 hr

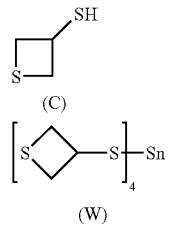

(C)

(W)

Example 6-A1

The compound of Preparative Example 1 was dissolved in 4-mercaptomethyl-1,8-dimercapto-3,6-dithiaoctane at 20° C. to satisfy the compositional ratios described in Table 6 and the refractive index (nD) was measured. The obtained physical property values are shown in Table 6.

Example 6-A2

In the same manner as in Example 6-A1 except for using the composition of Table 6, a mixed solution was prepared and the refractive index (nD) was measured. The obtained physical property values are shown in Table 6.

Examples 6-B1 to 6-B2

In the same manner as in Example 6-A1 except that the compound of Preparative Example 1 was changed to the compound of Preparative Example 2 and the composition of Table 6 was used, a mixed solution was prepared and the refractive index (nD) was measured. The obtained physical property values are shown in Table 6.

Comparative Example 6

In the same manner as in Example 6-A1 except that the compound of Preparative Example 1 was not used and 4-mercaptomethyl-1,8-dimercapto-3,6-dithiaoctane alone was used, a solution was prepared and the refractive index (nD) was measured. The obtained physical property values are shown in Table 6.

TABLE 6

| | Composition (% by weight) | | | Added materials ppm | Optical physical property Refractive index (nD) |
|---|---|---|---|---|---|
| | Compound of Preparative Example 1 | Compound of Preparative Example 2 | Thiol compound A | | |
| Comparative Example 6 | 0% | 0% | 100% | None | 1.630 |
| Example 6-A1 | 30% | 0% | 70% | None | 1.672 |
| Example 6-A2 | 47% | 0% | 53% | None | 1.700 |
| Example 6-B1 | 0% | 11% | 89% | DCH 1000 | 1.651 |
| Example 6-B2 | 0% | 20% | 80% | DCH 1000 | 1.668 |

A: 4-Mercaptomethyl-1,8-dimercapto-3,6-dithiaoctane
DCH: N,N-Dicyclohexylmethylamine

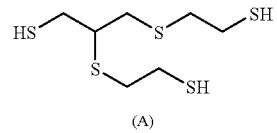 [SMILES: SCCSCC(CS)SCCS]

(A)

Example 7-A1

The compound (3 parts by weight) obtained in Preparative Example 3 was dissolved in 4-mercaptomethyl-1,8-dimercapto-3,6-dithiaoctane (48.5 parts by weight), and then dibutyltin dichloride (70 ppm) as a polymerization catalyst and m-xylylene diisocyanate (48.5 parts by weight) were mixed therewith to give a uniform solution. This mixed solution was degassed for 5 minutes under reduced pressure, and then charged into a mold composed of a glass mold and a tape. This mold was introduced to a polymerization oven, and slowly rised temperature from 25° C. to 120° C. over 20 hours to carry out polymerization. After the polymerization was completed, a mold was taken from the oven and released to obtain a molded body.

The values of the physical properties of the obtained molded body are shown in Table 7.

Examples 7-A2 to 7-A3

In the same manner as in Example 7-A1 except for using the composition of Table 7, a mixed solution and a molded body were prepared. The values of the physical properties of the obtained molded body are shown in Table 7.

Comparative Example 7

In the same manner as in Example 7-A1 except that the compound obtained in Preparative Example 3 was not used and the composition of Table 7 was used, a mixed solution and a molded body were prepared. The values of the physical properties of the obtained molded body are shown in Table 7.

Example 8-A1

The compound (5 parts by weight) obtained in Preparative Example 1 was dissolved in a mixture (47 parts by weight) of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane, and then m-xylylene diisocyanate (48 parts by weight) was further mixed therewith to give a uniform solution. This mixed solution was degassed for 5 minutes under reduced pressure, and then charged into a mold composed of a glass mold and a tape. This mold was introduced to a polymerization oven, and slowly rised temperature from 25° C. to 120° C. over 20 hours to carry out polymerization. After the polymerization was completed, a mold was taken from the oven and released to obtain a molded body.

The values of the physical properties of the obtained molded body are shown in Table 8.

Comparative Example 8

In the same manner as in Example 8-A1 except that the compound obtained in Preparative Example 1 was not used, dibutyltin dichloride as a polymerization catalyst was added at 50 ppm, and the composition of Table 8 was used, a mixed solution and a molded body were prepared. The values of the physical properties of the obtained molded body are shown in Table 8.

TABLE 7

|  | Composition (% by weight) | | | | Optical physical property | | | Heat resistance Tg (°C.) | Specific gravity |
|---|---|---|---|---|---|---|---|---|---|
|  | Compound of Preparative Example 3 | Thiol compound A | Isocyanate compound I-2 | Polymerization catalyst ppm | Refractive index (ne) | Abbe Number | Transparency | | |
| Comparative Example 7 | 0% | 50% | 50% | DBC 70 | 1.666 | 30.5 | Transparent | 80 | 1.36 |
| Example 7-A1 | 3% | 48.5% | 48.5% | DBC 70 | 1.668 | 30.6 | Transparent | 76 | 1.37 |
| Example 7-A2 | 6% | 47% | 47% | DBC 70 | 1.670 | 30.8 | Transparent | 71 | 1.38 |
| Example 7-A3 | 11% | 44.5% | 44.5% | DBC 70 | 1.673 | 31.3 | Transparent | 73 | 1.40 |

A: 4-Mercaptomethyl-1,8-dimercapto-3,6-dithiaoctane

I-2: m-Xylylene diisocyanate

DBC: Dibutyltin dichloride

Polymerization condition: (25° C.→120° C.)/16 hr→120° C./4 hr

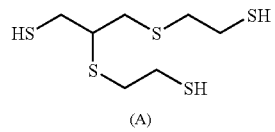 [SMILES: SCCSCC(CS)SCCS]

(A)

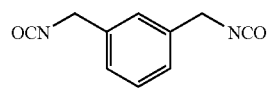

(I-2)

TABLE 8

| | Composition (% by weight) | | | | | Optical physical property | | | Heat resistance |
|---|---|---|---|---|---|---|---|---|---|
| | Compound of Preparative Example 1 | Thiol compound | Isocyanate compound | Polymerization catalyst | ppm | Refractive index (ne) | Abbe Number | Transparency | Tg (° C.) |
| Comparative Example 8 | 0% | 49% | 51% | DBC | 50 | 1.668 | 31.2 | Transparent | 101 |
| Example 8-A1 | 5% | 47% | 48% | None | | 1.675 | 30.7 | Transparent | 102 |

B: Mixture of 5,7-dimercaptomethyl-1,11-dimercapto-3,6,9-trithiaundecane, 4,7-dimercaptomethyl-1,11-dimercapto-3,6,9-trithiaundecane, and 4,8-dimetcaptomethyl-1,11-dimercapto-3,6,9-trithiaundecane
I-2: m-Xylylene diisocyanate
DBC: Dibutyltin dichloride
Polymerization condition: (25° C.→120° C.)/16 hr→120° C./4 hr

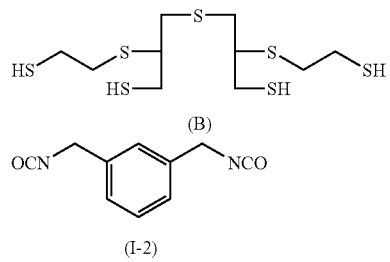

(B)

(I-2)

Example 9-A1

The compound (5 parts by weight) obtained in Preparative Example 1 was dissolved in a mixture (53 parts by weight) of 1,1,3,3-tetrakis(mercaptomethylthio)propane and 4,6-bis(mercaptomethylthio)-1,3-dithiane and 2-(2,2-bis(mercaptomethylthio)ethyl)-1,3-dithietane at 20° C., and then m-xylylene diisocyanate (42 parts by weight) was further mixed therewith to give a uniform solution. This mixed solution was degassed for 5 minutes under reduced pressure, and then charged into a mold composed of a glass mold and a tape. This mold was introduced to a polymerization oven, and slowly rised temperature from 35° C. to 100° C. over 34 hours to carry out polymerization. After the polymerization was completed, a mold was taken from the oven and released to obtain a molded body.

The values of the physical properties of the obtained molded body are shown in Table 9.

Example 9-B1

The compound (4 parts by weight) obtained in Preparative Example 3 was dissolved in a mixture (54 parts by weight) of 1,1,3,3-tetrakis(mercaptomethylthio)propane 4,6-bis(mercaptomethylthio)-1,3-dithiane, and 2-(2,2-bis(mercaptomethylthio)ethyl)-1,3-dithietane, and then m-xylylene diisocyanate (42 parts by weight) containing dibutyltin dichloride (60 ppm) as a polymerization catalyst was further mixed therewith to give a uniform solution. This mixed solution was degassed for 5 minutes under reduced pressure, and then charged into a mold composed of a glass mold and a tape. This mold was introduced to a polymerization oven, and slowly rised temperature from 35° C. to 100° C. over 34 hours to carry out polymerization. After the polymerization was completed, a mold was taken from the oven and released to obtain a molded body.

The values of the physical properties of the obtained molded body are shown in Table 9.

Examples 9-B2 to 9-B4

In the same manner as in Example 9-B1 except for using the composition of Table 9, a mixed solution and a molded body were prepared. The values of the physical properties of the obtained molded body are shown in Table 9.

Comparative Example 9

In the same manner as in Example 9-B1 except that the compound obtained in Preparative Example 1 or 3 was not used, a mixed solution and a molded body were prepared. The values of the physical properties of the obtained molded body are shown in Table 9.

TABLE 9

| | Composition (% by weight) | | | | | | | Optical physical property | | | Heat resistance |
|---|---|---|---|---|---|---|---|---|---|---|---|
| | Compound 1 Preparative Example 1 | Compound of Preparative Example 3 | Thiol compound D | Isocyanate compound I-2 | Polymerization catalyst | ppm | | Refractive index (ne) | Abbe Number | Transparency | Tg (° C.) |
| Comparative Example 9 | 0% | 0% | 56% | 44% | DBC | 60 | | 1.696 | 30.1 | Transparent | 97 |
| Example 9-A1 | 5% | 0% | 53% | 42% | None | | | 1.701 | 29.5 | Transparent | 101 |

TABLE 9-continued

| | Composition (% by weight) | | | | | | Optical physical property | | | Heat resistance |
|---|---|---|---|---|---|---|---|---|---|---|
| | Compound 1 Preparative Example 1 | Compound of Preparative Example 3 | Thiol compound D | Isocyanate compound I-2 | Polymerization catalyst | ppm | Refractive index (ne) | Abbe Number | Trans- parency | Tg (° C.) |
| Example 9-B1 | 0% | 4% | 54% | 42% | DBC | 60 | 1.697 | 29.8 | Transparent | 87 |
| Example 9-B2 | 0% | 5% | 53% | 42% | DBC | 60 | 1.699 | 29.8 | Transparent | 81 |
| Example 9-B3 | 0% | 8% | 51% | 41% | DBC | 60 | 1.701 | 29.7 | Transparent | ND |
| Example 9-B4 | 0% | 10% | 50% | 40% | DBC | 60 | 1.702 | 29.3 | Transparent | ND |

D: Mixture of 1,1,3,3-tetrakis(mercaptomethylthio)propane and 4,6-bis(mercaptomethylthio)-1,3-dithiane and 2-(2,2-bis(mercaptomethylthio)ethyl)-1,3-dithietane
I-2: m-Xylylene diisocyanate
DBC: Dibutyltin dichloride
Polymerization condition: (35→100° C./30 hr)→100° C./4 hr

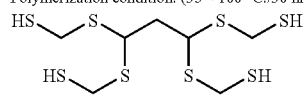

(D)

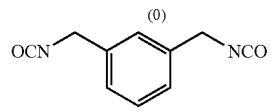

(I-2)

Example 10-A1

The compound (6 parts by weight) of Preparative Example 3 was added to and dissolved in a mixture (9 parts by weight) of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane, in which N,N-dimethylcyclohexylamine (80 ppm relative to the epithio compound) and N,N-dicyclohexylmethylamine (400 ppm relative to the epithio compound) had been dissolved, and bis(2,3-epithiopropyl)disulfane (85 parts by weight) to give a uniform solution. This solution was degassed for 5 minutes at 400 Pa, and then charged into a mold composed of a glass mold and a tape. This mold was introduced to a polymerization oven, and slowly rised temperature from 30° C. to 80° C. over 33 hours to carry out polymerization. After the polymerization was completed, a mold was taken from the oven and released to obtain a molded body.

The values of the physical properties of the obtained molded body are shown in Table 10.

Example 10-A2

In the same manner as in Example 10-A1 except for using the composition of Table 10, a mixed solution and a molded body were prepared. The values of the physical properties of the obtained molded body are shown in Table 10.

Comparative Example 10

In the same manner as in Example 10-A1 except that the compound obtained in Preparative Example 3 was not used and the composition of Table 10 was used, a mixed solution and a molded body were prepared. The values of the physical properties of the obtained molded body are shown in Table 10.

TABLE 10

| | Composition (% by weight) | | | Polymerization catalyst | | Optical physical property | | | Heat resistance | Specific gravity |
|---|---|---|---|---|---|---|---|---|---|---|
| | Compound of Preparative Example 3 | Thiol compound B | Epithio compound X | ppm | ppm | Refractive index (ne) | Abbe Number | Transparency | Tg (° C.) | |
| Comparative Example 10 | 0% | 9% | 91% | Cat-1 400 | Cat-2 80 | 1.737 | 32.3 | Transparent | 73 | 1.47 |

TABLE 10-continued

| | Composition (% by weight) | | | Polymerization catalyst | | | | Optical physical property | | Transparency | Heat resistance Tg (° C.) | Specific gravity |
|---|---|---|---|---|---|---|---|---|---|---|---|---|
| | Compound of Preparative Example 3 | Thiol compound B | Epithio compound X | | ppm | | ppm | Refractive index (ne) | Abbe Number | | | |
| Example 10-A1 | 6% | 9% | 85% | Cat-1 | 400 | Cat-2 | 80 | 1.740 | 31.5 | Transparent | 73 | 1.49 |
| Example 10-A2 | 11% | 8% | 81% | Cat-1 | 400 | Cat-2 | 80 | 1.744 | 30.6 | Transparent | 71 | 1.50 |

B: Mixture of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane
X: Bis(2,3-epithiopropyl)disulfane
Cat-1: N,N-Dicyclohexylmethylamine
Ca-2: N,N-Dimethylcyclohexylamine
Polymerization condition: 30° C./12 hr→(30→80/17 hr)→80° C./4 hr

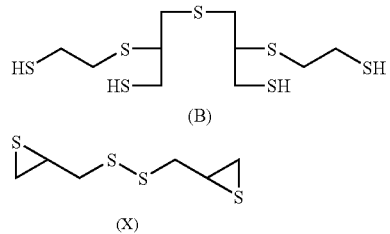

(B)

(X)

Example 11-A1

3-Mercaptothietane (18 parts by weight), tetrakis(3-thietanylthio)tin (73 parts by weight), and the compound (9 parts by weight) of Preparative Example 3 were heated and mixed at 70° C. to give a uniform solution. This solution was degassed for 5 minutes at 400 Pa, and then charged into a mold composed of a glass mold and a tape. This mold was introduced to a polymerization oven, and slowly rised temperature from 70° C. to 130° C. over 68 hours to carry out polymerization. After the polymerization was completed, a mold was taken from the oven and released to obtain a molded body.

The values of the physical properties of the obtained molded body are shown in Table 11.

Examples 11-A2 to 11-A3

In the same manner as in Example 11-A1 except for using the composition of Table 11, a mixed solution and a molded body were prepared. The values of the physical properties of the obtained molded body are shown in Table 11.

Examples 11-B1 to 11-B3

In the same manner as in Example 11-A1 except that the compound of Preparative Example 3 was changed to the compound of Preparative Example 4 and the composition of Table 11 was used, a mixed solution and a molded body were prepared. The values of the physical properties of the obtained molded body are shown in Table 11.

Comparative Example 11

In the same manner as in Example 11-A1 except that the compound obtained in Preparative Example 3 or 4 was not used and the composition of Table 11 was used, a mixed solution and a molded body were prepared. The values of the physical properties of the obtained molded body are shown in Table 11.

TABLE 11

| | Composition (% by weight) | | | | | Optical physical property | | | Heat resistance Tg (° C.) | Specific gravity |
|---|---|---|---|---|---|---|---|---|---|---|
| | Compound of Preparative Example 3 | Compound of Preparative Example 4 | Thiol Compound C | Metal thietane W | Added materials | Refractive index (ne) | Abbe Number | Transparency | | |
| Comparative Example 11 | 0% | 0% | 20% | 80% | None | 1.776 | 26.4 | Transparent | 107 | 1.68 |
| Example 11-A1 | 9% | 0% | 18% | 73% | None | 1.778 | 26.7 | Transparent | 97 | ND |
| Example 11-A2 | 17% | 0% | 17% | 66% | None | 1.779 | 26.7 | Transparent | 96 | ND |
| Example 11-A3 | 21% | 0% | 16% | 63% | None | 1.780 | 26.9 | Transparent | 73 | ND |
| Example 11-B1 | 0% | 9% | 18% | 73% | None | 1.789 | 24.8 | Transparent | 110 | 1.73 |

TABLE 11-continued

| | Composition (% by weight) | | | | Optical physical property | | | Heat resistance Tg (° C.) | Specific gravity |
|---|---|---|---|---|---|---|---|---|---|
| | Compound of Preparative Example 3 | Compound of Preparative Example 4 | Thiol Compound C | Metal thietane W | Added materials | Refractive index (ne) | Abbe Number | Transparency | | |
| Example 11-B2 | 0% | 17% | 17% | 66% | None | 1.802 | 23.4 | Transparent | 113 | 1.77 |
| Example 11-B3 | 0% | 22% | 16% | 62% | None | 1.816 | 23.0 | Transparent | 119 | 1.81 |

C: 3-Mercaptothietane
W: Tetrakis(3-thietanylthio)tin
Polymerization condition: 70° C./36 hr→(70→130° C./8 hr)→130° C./24 hr

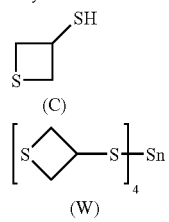

The invention claimed is:

1. An additive for a polymerizable composition containing a compound represented by the following general formula (a)

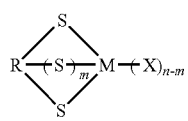

(a)

wherein R represents a saturated hydrocarbon group having 1 to 3 carbon atoms, M represents Sn, Sb, Bi, or Ge, m represents 0 or 1, R and M are not directly bonded when m is 0, n represents an integer of 1 to 3, X represents an alkylsulfanyl group having 1 to 3 carbon atoms or a group represented by the following general formula (1a)

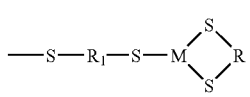

(1a)

wherein M represents Sn, Sb, or Bi, R represents an alkylene group having 1 to 3 carbon atoms, a plurality of X may be the same as or different from each other, and wherein if two or more linking groups X are bonded with the metal atom M, the linking groups X may combine together to form a ring.

2. The additive for a polymerizable composition as set forth in claim 1, wherein said compound represented by the general formula (a) is represented by the following general formula (1)

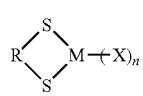

(1)

wherein M represents Sn, Sb, or Bi, R represents an alkylene group having 1 to 3 carbon atoms, n and X are the same as in said general formula (a).

3. The additive for a polymerizable composition as set forth in claim 2, wherein said compound represented by the general formula (1) is represented by the following general formula (2) or (3)

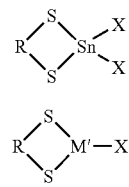

(2)

(3)

wherein R and X are the same as in the general formula (1), in the general formula (2), the two linking groups X may form a ring, and in the general formula (3), M' represents Sb or Bi.

4. The additive for a polymerizable composition as set forth in claim 2, wherein R is an alkylene group having 2 or 3 carbon atoms.

5. The additive for a polymerizable composition as set forth in claim 4, wherein said compound represented by the general formula (2) is represented by the following general formula (4) or (5)

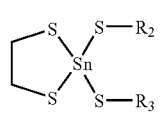

(4)

(5)

wherein $R_2$ and $R_3$ each independently represent an alkyl group having 1 to 3 carbon atoms, and in the general formula (5), A represents a ring structure.

6. The additive for a polymerizable composition as set forth in claim 5, wherein said compound represented by the general formula (5) is represented by the following general formula (5a) or (5b)

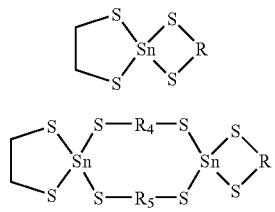

(5a)

(5b)

wherein R is the same as in the general formula (1), and in the general formula (5b), $R_4$ and $R_5$ represent an alkylene group having 1 to 3 carbon atoms, and may be the same as or different from each other.

7. The additive for a polymerizable composition as set forth in claim 6, wherein said compound represented by the general formula (5a) is represented by the following chemical formula

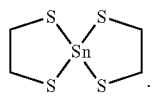

8. The additive for a polymerizable composition as set forth in claim 4, wherein said compound represented by the general formula (3) is represented by the following general formula (6)

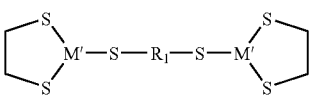

(6)

wherein M' represents Sb or Bi, and $R_1$ represents an alkylene group having 1 to 3 carbon atoms.

9. The additive for a polymerizable composition as set forth in claim 8, wherein M' is Sb.

10. The additive for a polymerizable composition as set forth in claim 9, wherein said compound represented by the general formula (6) is represented by the following chemical formula

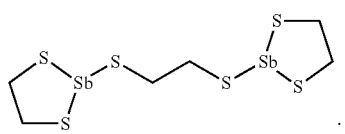

11. The additive for a polymerizable composition as set forth in claim 1, wherein said compound represented by the general formula (a) is represented by the following general formula (9)

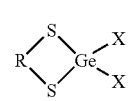

(9)

wherein R represents an alkylene group having 1 to 3 carbon atoms, and X is the same as in the general formula (a).

12. The additive for a polymerizable composition as set forth in claim 11, wherein said compound represented by the general formula (9) is represented by the following general formula (10) or (11),

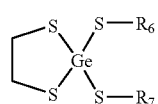

(10)

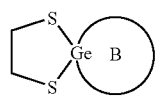

(11)

wherein $R_6$ and $R_7$ each independently represent an alkyl group having 1 to 3 carbon atoms, and in the general formula (11), B represents a ring structure.

13. The additive for a polymerizable composition as set forth in claim 12, wherein said compound represented by the general formula (11) is represented by the following general formula (11a) or (11b)

(11a)

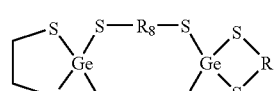

(11b)

wherein R is the same as in the general formula (9), and in the general formula (11b), $R_8$ and $R_9$ represent an alkylene group having 1 to 3 carbon atoms, and may be the same as or different from each other.

14. The additive for a polymerizable composition as set forth in claim 13, wherein said compound represented by the general formula (11a) is represented by the following chemical formula

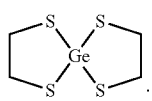

15. The additive for a polymerizable composition as set forth in claim 1, wherein said compound represented by the general formula (a) is represented by the following chemical formula

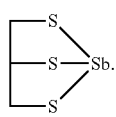

16. A polymerizable composition, wherein the additive for a polymerizable composition as set forth in claim 1 is blended.

17. The polymerizable composition as set forth in claim 16, wherein a thiol compound is further blended.

18. The polymerizable composition as set forth in claim 17, wherein said thiol compound contains at least one selected from the group consisting of 3-mercaptothietane, 1,2-ethanedithiol, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 1,1,3,3-tetrakis(mercaptomethylthio)propane, 4,6-bis(mercaptomethylthio)-1,3-dithiane, 2-(2,2-bis(mercaptomethylthio)ethyl)-1,3-dithietane, and 2,5-bis(mercaptomethyl)-1,4-dithiane.

19. The polymerizable composition as set forth in claim 18, wherein a polymerizable compound is further blended.

20. The polymerizable composition as set forth in claim 19, wherein said polymerizable compound comprises at least one selected from the group consisting of an isocyanate compound, an episulfide compound, an epoxy compound, and a thietane compound.

21. A resin obtained by polymerization of the polymerizable composition as set forth in claim 16.

22. A transparent member comprising the resin as set forth in claim 21.

23. An optical component comprising the transparent member as set forth in claim 22.

* * * * *